(12) United States Patent
Sinha et al.

(10) Patent No.: US 12,390,571 B2
(45) Date of Patent: Aug. 19, 2025

(54) NEEDLE DISLODGEMENT DETECTION SYSTEMS AND METHODS

(71) Applicants: Fresenius Medical Care Holdings, Inc., Waltham, MA (US); AWE Technologies LLC, Bay Shore, NY (US); Fresenius Medical Care Deutschland GmbH, Bad Homburg (DE)

(72) Inventors: Dipen N. Sinha, Bay Shore, NY (US); Robert Schaefer, Bay Shore, NY (US); Curtis Osterhoudt, Hesperus, CO (US); Peter G. Espina, Bay Shore, NY (US); Martin J. Crnkovich, Walnut Creek, CA (US); Fei Wang, Concord, CA (US); Steve M. Bowman, Essex, MA (US); Martin Urban, Thuengersheim (DE)

(73) Assignees: AWE Technologies LLC, Bay Shore, NY (US); Fresenius Medical Care Deutschland GmbH, Bad Homburg (DE); Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 18/925,370

(22) Filed: Oct. 24, 2024

(65) Prior Publication Data

US 2025/0135082 A1 May 1, 2025

Related U.S. Application Data

(60) Provisional application No. 63/593,653, filed on Oct. 27, 2023.

(51) Int. Cl.
*A61M 1/36* (2006.01)
*A61M 1/16* (2006.01)

(52) U.S. Cl.
CPC ........ *A61M 1/3656* (2014.02); *A61M 1/1601* (2014.02)

(58) Field of Classification Search
CPC .............. A61M 1/3656; A61M 1/3639; A61M 1/1601; A61M 2250/15; A61M 2250/17;
(Continued)

(56) References Cited

U.S. PATENT DOCUMENTS

| 4,607,520 A | 8/1986 | Dam |
| 4,923,598 A | 5/1990 | Schal |

(Continued)

FOREIGN PATENT DOCUMENTS

WO 2021053201 A1 3/2021

OTHER PUBLICATIONS

International Preliminary Report on Patentability, PCT/US2021/039744, dated Dec. 13, 2022, 7 Pages.
(Continued)

*Primary Examiner* — Philip R Wiest
(74) *Attorney, Agent, or Firm* — Potomac Law Group, PLLC

(57) ABSTRACT

This disclosure teaches a system and method for monitoring an extracorporeal blood circuit of a patient and identifying a needle dislodgement. The method includes identifying a potential needle dislodgement event based on changes in pressure of the extracorporeal blood circuit, searching for a heart rate of a patient by analyzing an optical backscatter signal from an optical sensor attached to the extracorporeal blood circuit or by analyzing a pressure signal representative of the pressure in the extracorporeal blood circuit, and verifying the potential needle dislodgement event is a needle dislodgement based on the absence of the heart rate.

16 Claims, 28 Drawing Sheets

(58) Field of Classification Search
CPC .......... A61M 2250/18; A61M 2250/50; A61M 2250/3331; A61M 2250/3334
See application file for complete search history.

(56) References Cited

U.S. PATENT DOCUMENTS

| | | |
|---|---|---|
| 8,535,522 B2 | 9/2013 | Fulkerson et al. |
| 10,940,252 B2 | 3/2021 | Toyoda et al. |
| 2002/0091350 A1 | 7/2002 | Belson |
| 2007/0219597 A1 | 9/2007 | Kamen et al. |
| 2009/0082676 A1 | 3/2009 | Bennison |
| 2012/0150091 A1 | 6/2012 | Roger et al. |
| 2012/0271160 A1 | 10/2012 | Buckberry |
| 2012/0271161 A1 | 10/2012 | Buckberry |
| 2012/0289928 A1 | 11/2012 | Wright et al. |
| 2013/0204174 A1* | 8/2013 | Olde ................... A61M 1/3653 604/6.11 |
| 2014/0262252 A1 | 9/2014 | Slepicka et al. |
| 2017/0108471 A1 | 4/2017 | Sturtevant et al. |
| 2017/0173253 A1 | 6/2017 | Funkhouser |
| 2019/0217030 A1 | 7/2019 | Burgess et al. |

OTHER PUBLICATIONS

International Search Report and Written Opinion for International Application No. PCT/US2021/039744 dated Oct. 13, 2021.
International Search Report and Written Opinion mailed Feb. 3, 2025 for International Patent Application No. PCT/US2024/052736.

* cited by examiner

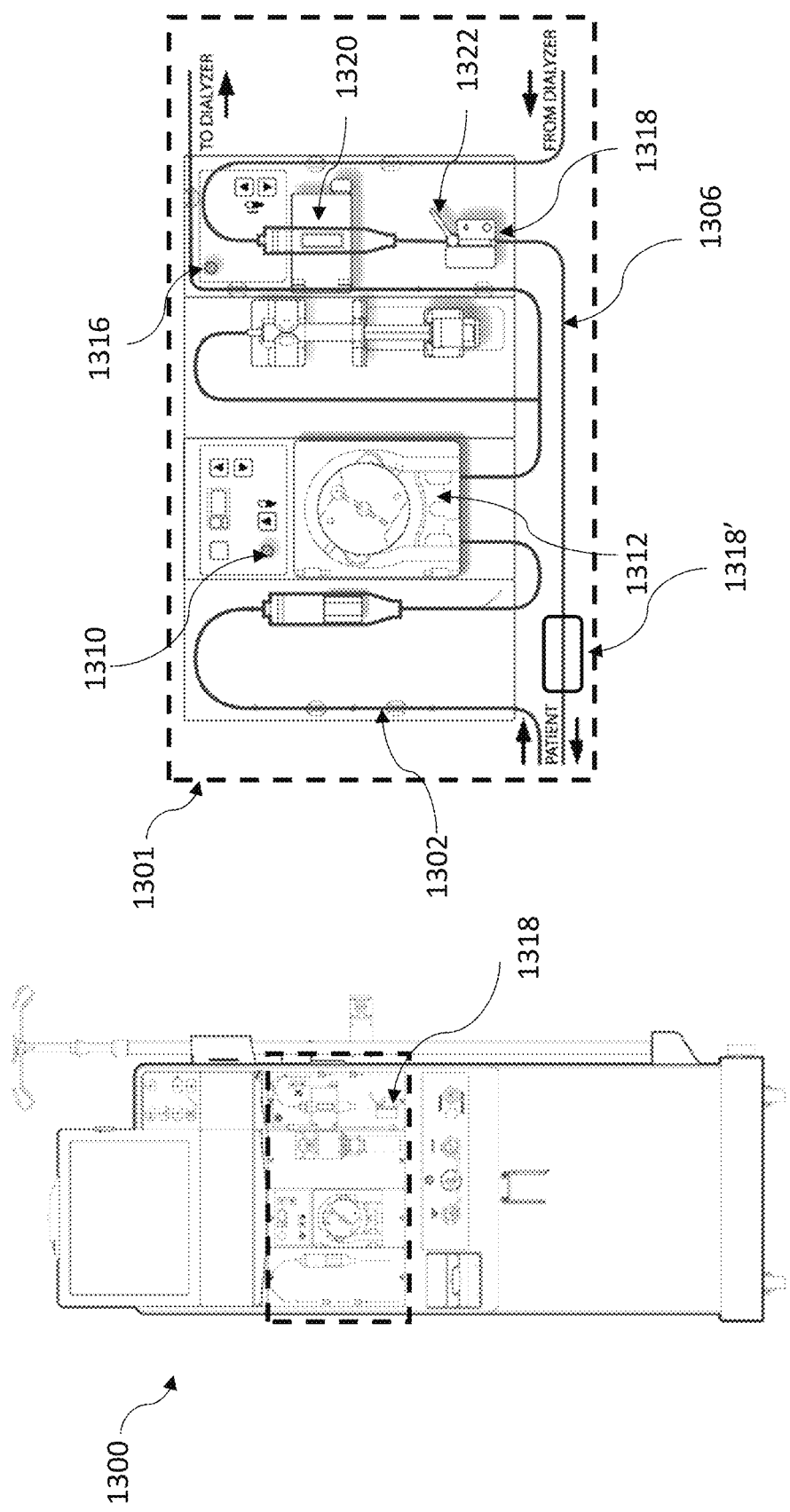

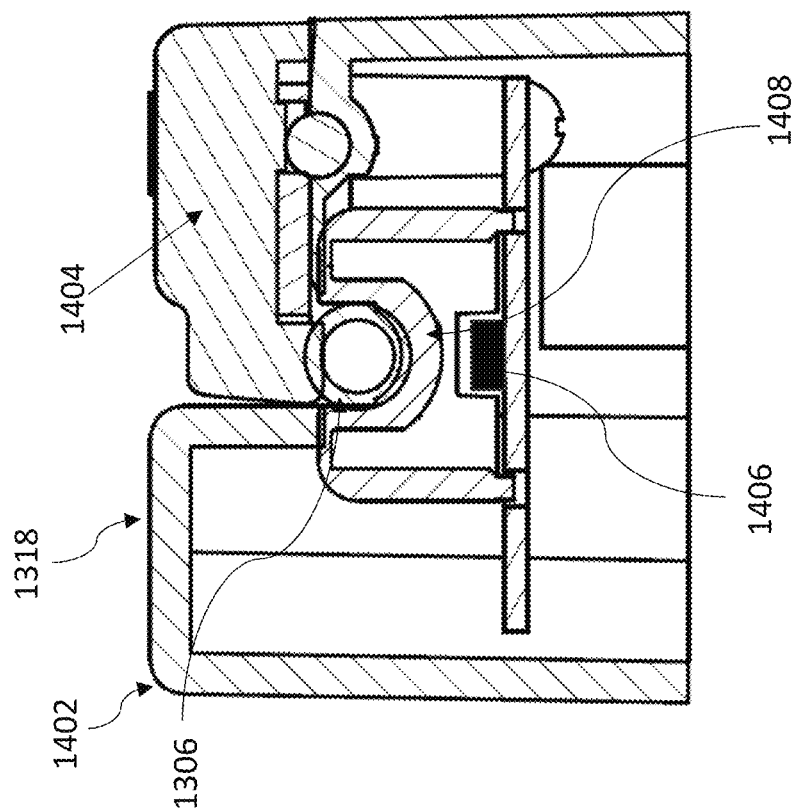
FIG. 14C
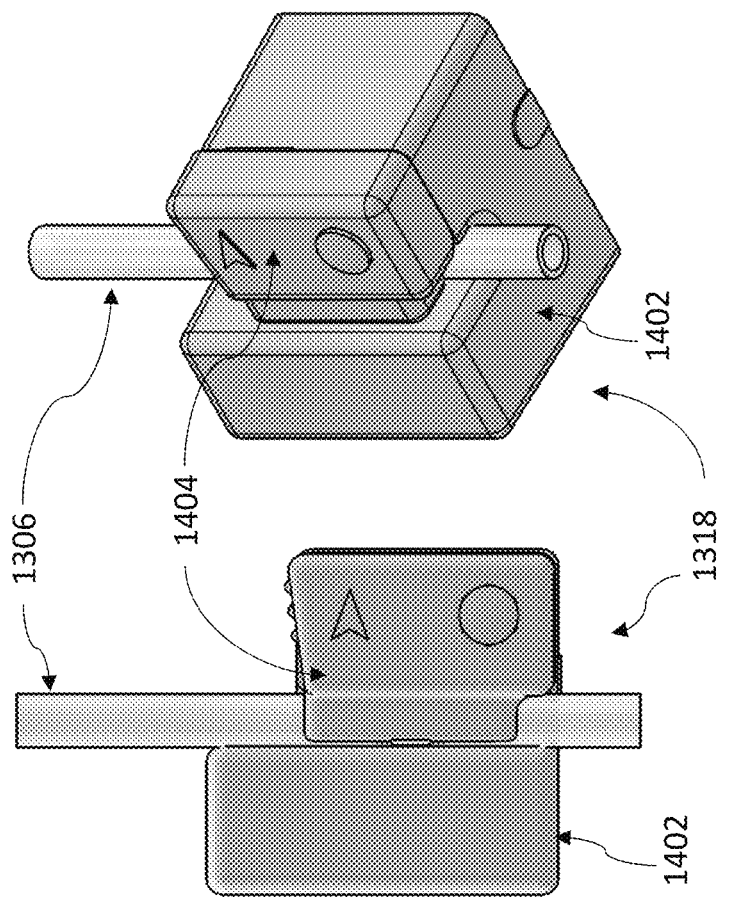
FIG. 14B
FIG. 14A

NEEDLE DISLODGEMENT DETECTION SYSTEMS AND METHODS

CROSS-REFERENCE TO RELATED APPLICATION

This application claims the benefit of priority to U.S. Provisional Patent Application Ser. No. 63/593,653, filed on Oct. 27, 2023, which is incorporated by reference in its entirety as if fully set forth herein.

TECHNICAL FIELD

The present disclosure generally relates to monitoring extracorporeal blood circuits. Particularly, but not exclusively, the present disclosure relates to methods and systems for monitoring extracorporeal blood circuits and identifying needle dislodgements.

BACKGROUND

Various devices are known in the field of medicine with which it is possible to remove fluids from the patient or supply fluids to the patient via a tube. Access to the patient is generally gained with a catheter inserted into bodily organs or with a cannula for puncturing blood vessels. Proper access to the patient must be ensured during the extracorporeal treatment. Therefore, it is necessary to monitor the patient's access.

Extracorporeal blood treatment devices, in particular those that involve an extracorporeal blood flow require proper access to the patient. Some extracorporeal blood treatment devices include, for example, dialysis systems and cell separators that require access to the vascular system of the patient. During extracorporeal blood treatment, blood is removed from the patient for instance using an arterial tube with an arterial puncture cannula, and the blood is re-supplied to the patient via a venous tube with a venous puncture cannula.

Needle dislodgement during an extracorporcal blood treatment (e.g., dialysis) is a rare event. However, if needle dislodgement is not detected quickly, particularly venous needle dislodgement (VND) it can lead to fatal blood loss in only a few minutes. For example, patients with a normal blood volume of 3-5 L subjected to the normal extracorporeal blood flow rate of 200-500 ml/min during dialysis, will likely suffer from fatal blood loss within 2-5 minutes after a VND. The reported number of VNDs per treatment falls within a wide range, from 0.0008% to 0.1% with an estimate that 10-33% of the VNDs lead to death.

A number of different access monitoring devices that function based on different principles have been developed and implemented. But these conventional approaches suffer from a number of shortcomings. In some such conventional approaches, the venous line pressure is measured in various ways to try to detect a VND based on an abrupt decrease in the venous line pressure. However, such pressure-monitoring approaches are not robust because sometimes a VND or partial VND leads to only a small pressure change in the venous return line. Conventional pressure monitoring systems with sufficient sensitivity to detect such small pressure changes have been utilized, but such systems require sufficient damping or averaging to reduce noise in the measurement, which would otherwise adversely affect the systems' response time. Moreover, these systems typically suffer from many false positives, thus increasing the burden of monitoring and addressing false alarms. Another approach is to place wetness detectors at or near a patient's access point, which would send an alert after blood has leaked and collected at the detector. Wetness detectors are also less than optimal because a misplaced detector can defeat such a system and the path of a leak cannot always be reliably predicted. Mechanical tube constriction devices are also less than optimal because of the potential for improper implementation.

A need exists for a reliable, robust, and cost-effective solution for detecting needle dislodgements, in particular, venous needle dislodgements for extracorporeal blood treatments.

BRIEF SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

The present disclosure describes needle dislodgement detection systems and methods that address conventional shortcomings. For example, the systems according to the present disclosure can provide a more reliable, robust, rapid, and cost-effective solution for detecting needle dislodgements.

In one example, a method of monitoring an extracorporeal blood circuit of a patient and identifying a needle dislodgement comprises identifying a potential needle dislodgement event based on changes in pressure of the extracorporeal blood circuit; searching for a heart rate of a patient by analyzing an optical backscatter signal from an optical sensor attached to the extracorporeal blood circuit; and verifying the potential needle dislodgement event is a needle dislodgement based on the absence of the heart rate. Alternatively or additionally to any of the examples above, the method can further include reducing a speed of a blood pump for the extracorporeal blood circuit when the potential needle dislodgement event is identified; and searching for the heart rate of the patient while the blood pump is at the reduced speed. Alternatively or additionally to any of the examples above, the speed of the blood pump can be reduced to a blood flow rate of between about 50-120 mL/min or about 100-170 mL/min when the potential needle dislodgement event is identified. Alternatively or additionally to any of the examples above, the method can further include verifying the potential needle dislodgement event is not a needle dislodgement based on the presence of the heart rate of the patient. Alternatively or additionally to any of the examples above, the method can include returning the blood pump to a previous speed following verification that the potential needle dislodgement event is not a needle dislodgement. Alternatively or additionally to any of the examples above, the potential needle dislodgement event can be identified by an algorithm that calculates a needle dislodgement value based on a maximum arterial pressure difference, a venous pressure change, the arterial pressure, and venous pressure, and when the needle dislodgement value is below a threshold value the algorithm identifies the potential needle dislodgement event. Alternatively or additionally to any of the examples above, the optical backscatter signal can be representative of the detected backscatter of RED wavelength light energy. Alternatively or additionally to any of the examples above, the heart rate of the patient can be searched for using an algorithm that analyzes the optical backscatter signal by: filtering data from the optical backscatter signal to produce filtered optical backscatter data (FOBD); computing a peak to peak (PTP) value by subtracting min FOBD from max FOBD; computing a prominence value based on PTP value; identifying and indexing peaks from the FOBD with a prominence above a prominence threshold (PT) and a distance between each peak above a minimum peak distance (min PD); calculating peak times when more than one peak is indexed; and calculating the heart rate based on the peak times. Alternatively or additionally to any of the examples above, the method can further include verifying the potential needle dislodgement event is not a needle dislodgement based on the presence of the heart rate (HR) within a set HR range, a variance of the FOBD within a set variance range, and a blood pump rate (BPR) within a set BPR range. Alternatively or additionally to any of the examples above, the method can further include identifying an arterial heart rate of the patient by analyzing changes in the arterial pressure of the extracorporeal blood circuit, wherein the set HR range is determined based on the identified arterial heart rate. Alternatively or additionally to any of the examples above, verifying the potential needle dislodgement event can be further based on the presence of the arterial heart rate within a set arterial HR range. Alternatively or additionally to any of the examples above, the optical sensor can be attached to a venous line of the extracorporeal blood circuit and the needle dislodgement is a venous needle dislodgement.

In another example, a system for detecting a needle dislodgement of an extracorporeal blood circuit of a patient comprises a computing device; a processor; a memory comprising instructions, when executed by the processor cause the system to: receive a venous pressure signal, an arterial pressure signal, and an optical backscatter signal from an optical sensor attached to a venous line of the extracorporeal blood circuit; identify a potential needle dislodgement event based on changes in the arterial pressure signal and the venous pressure signal; search for a heart rate of the patient by analyzing the optical backscatter signal; and verify the potential needle dislodgement event is a needle dislodgement based on the absence of the heart rate.

Alternatively or additionally to any of the examples above, the memory comprising instructions, when executed by the processor can cause the system to: reduce a speed of a blood pump for the extracorporeal blood circuit when the potential needle dislodgement event is identified; and search for the heart rate of the patient while the blood pump is at the reduced speed. Alternatively or additionally to any of the examples above, the speed of the blood pump can be reduced to a blood flow rate between about 50-120 mL/min or about 100-170 mL/min when the potential needle dislodgement event is identified. Alternatively or additionally to any of the examples above, the memory comprising instructions, when executed by the processor can cause the system to verify the potential needle dislodgement event is not a needle dislodgement based on the presence of the heart rate. Alternatively or additionally to any of the examples above, the memory comprising instructions, when executed by the processor can cause the system to return the blood pump to a previous speed following verification that the potential needle dislodgement event is not a needle dislodgement. Alternatively or additionally to any of the examples above, the memory comprising instructions, when executed by the processor can cause an algorithm to calculate a needle dislodgement value based on a maximum arterial pressure difference, a venous pressure change, an arterial pressure, and a venous pressure, and when the needle dislodgement value is below a threshold value the algorithm identifies the potential needle dislodgement event. Alternatively or additionally to any of the examples above, the optical backscatter signal can be representative of the detected backscatter of RED wavelength light energy. Alternatively or additionally to any of the examples above, the memory comprising instructions, when executed by the processor can cause an algorithm to search for the heart rate of the patient by analyzing the optical backscatter signal, the steps of the algorithm comprise: filtering data from optical backscatter signal to produce filtered optical backscatter data (FOBD); computing a peak to peak (PTP) value by subtracting min FOBD from max FOBD; computing a prominence value based on PTP value; identifying and indexing peaks from the FOBD with a prominence above a prominence threshold (PT) and a distance between each peak above a minimum peak distance (min PD); calculating peak times when more than one peak is indexed; and calculating the heart rate based on the peak times. Alternatively or additionally to any of the examples above, the memory comprising instructions, when executed by the processor, can cause the system to verify the potential needle dislodgement event is not a needle dislodgement based on the presence of the heart rate (HR) within a set HR range, a variance of the FOBD within a set variance range, and a blood pump rate (BPR) within a set BPR range. Alternatively or additionally to any of the examples above, the optical sensor can be attached to a venous line of the extracorporeal blood circuit and the needle dislodgement is a venous needle dislodgement.

In another example, a computer-readable memory storage device of a needle dislodgement detection system for monitoring an extracorporeal blood circuit of a patient, comprises instructions, which when executed by a processor, cause the needle dislodgement detection system to: receive venous pressure data, arterial pressure data, and optical backscatter data from an optical sensor attached to a venous line of the extracorporeal blood circuit; identify a potential needle dislodgement event based on changes in the arterial pressure and the venous pressure; search for a heart rate of a patient by analyzing the optical backscatter signal; and verify the potential needle dislodgement event is a needle dislodgement based on the absence of the heart rate.

In another example, a dialysis machine comprises a blood pump; an extracorporeal blood circuit configured to connect the blood pump and a dialyzer to a patient; an arterial pressure monitor and a venous pressure monitor; an optical sensor attached to a venous line of the extracorporeal blood circuit; a computing device comprising a processor and a memory, the computing device being configured to: receive a venous pressure signal from the venous pressure monitor, an arterial pressure signal from the arterial pressure monitor, and an optical backscatter signal from the optical sensor; identify a potential needle dislodgement event based on changes in the arterial pressure and venous pressure; search for a heart rate of a patient by analyzing the optical backscatter signal; and verify the potential needle dislodgement event is a needle dislodgement based on the absence of the heart rate.

Alternatively or additionally to any of the examples above, the computing device can be configured to: reduce a speed of a blood pump for the extracorporeal blood circuit when the potential needle dislodgement event is identified; and search for the heart rate of the patient while the blood pump is at the reduced speed. Alternatively or additionally to any of the examples above, the speed of the blood pump can be reduced to between about 50-120 mL/min or about 100-170 mL/min when the potential needle dislodgement event is identified. Alternatively or additionally to any of the examples above, the computing device can be configured to verify the potential needle dislodgement event is not a needle dislodgement based on the presence of the heart rate. Alternatively or additionally to any of the examples above, the computing device can be configured to return the blood pump to a previous speed following verification that the potential needle dislodgement event is not a needle dislodgement. Alternatively or additionally to any of the examples above, the computing device can be configured to execute a needle dislodgement algorithm that calculates a needle dislodgement value based on a maximum arterial pressure difference, a venous pressure change, an arterial pressure, and a venous pressure, and when the needle dislodgement value is below a threshold value the computing device identifies the potential needle dislodgement event. Alternatively or additionally to any of the examples above, the optical backscatter signal can be representative of the detected backscatter of RED wavelength light energy. Alternatively or additionally to any of the examples above, the heart rate of the patient can be searched for using an algorithm that analyzes the optical backscatter signal by: filtering data from optical backscatter signal to produce filtered optical backscatter data (FOBD); computing a peak to peak (PTP) value by subtracting min FOBD from max FOBD; computing a prominence value based on PTP value; identifying and indexing peaks from the FOBD with a prominence above a prominence threshold (PT) and a distance between each peak above a minimum peak distance (min PD); calculating peak times when more than one peak is indexed; and calculating the heart rate based on the peak times. Alternatively or additionally to any of the examples above, the needle dislodgement is a venous needle dislodgement.

In another example, a method of identifying a potential needle dislodgement of an extracorporcal blood circuit based on arterial pressure data and venous pressure data, comprises: filtering the arterial pressure data and the venous pressure data to reduce noise; calculating current filtered arterial pressure data values (FAPD) based on at least three arterial pressure data values; calculating current filtered venous pressure data (FVPD) value based on at least three venous pressure data values; storing a queue of the current FAPD values and a discrete set of the current FVPD values; calculating a maximum arterial pressure (MAD) difference from the queue of stored current FAPD values; calculating a venous pressure change (VPC) that is the difference between the current FVPD minus the average FVPD of the queue of current FVPD; calculating a venous dislodgement value based on the VPC, the MAD, the current FAPD, and the current FVPD; and identifying a potential needle dislodgement when the venous dislodgement value is below a set threshold.

Alternatively or additionally to any of the examples above, the method further includes identifying an arterial heart rate of the patient by analyzing changes in the arterial pressure of the extracorporeal blood circuit, wherein filtering of the venous pressure data includes utilizing a lock-in signal processing technique based on the arterial heart rate.

In another example, a method of identifying and calculating a heart rate of a patient by analyzing an optical backscatter signal from an optical sensor attached to an extracorporcal blood circuit for the patient, comprises: filtering data from optical backscatter signal to produce filtered optical backscatter data (FOBD); computing a peak to peak (PTP) value by subtracting min FOBD from max FOBD; computing a prominence value based on PTP value; identifying and indexing peaks from the FOBD with a prominence above a prominence threshold (PT) and a distance between each peak above a minimum peak distance (min PD); calculating peak times when more than one peak is indexed; and calculating the heart rate based on the peak times.

Alternatively or additionally to any of the examples above, the method further includes reducing a speed of a blood pump for the extracorporeal blood circuit to a blood flow rate between about 50 mL/min and 120 mL/min or between about 100 to 170 mL/min prior to identifying and calculating the heart rate of the patient.

In another example, a method of identifying and calculating a heart rate of a patient connected to an extracorporeal blood circuit by analyzing a pressure signal from a pressure monitor attached to the extracorporeal blood circuit, comprises: filtering data from the pressure signal to produce filtered pressure data (FPD); computing a peak to peak (PTP) value by subtracting min FPD from max FPD; computing a prominence value based on PTP value; identifying and indexing peaks from the FPD with a prominence above a prominence threshold (PT) and a distance between each peak above a minimum peak distance (min PD); calculating peak times when more than one peak is indexed; and calculating the heart rate based on the peak times.

In another example, a method of monitoring an extracorporeal blood circuit of a patient and identifying a needle dislodgement, comprises: identifying a potential needle dislodgement event based on changes in pressure of the extracorporeal blood circuit; searching for a heart rate of a patient by analyzing changes in the pressure of the extracorporeal blood circuit; and verifying the potential needle dislodgement event is a needle dislodgement based on the absence of the heart rate; wherein the heart rate of the patient is searched for by analyzing a pressure signal from a pressure monitor attached to the extracorporeal blood circuit, the steps of which include: filtering data from the pressure signal to produce filtered pressure data (FPD); computing a peak to peak (PTP) value by subtracting min FPD from max FPD; computing a prominence value based on PTP value; identifying and indexing peaks from the FPD with a prominence above a prominence threshold (PT) and a distance between each peak above a minimum peak distance (min PD); calculating peak times when more than one peak is indexed; and calculating the heart rate based on the peak times.

In another example, a method of monitoring an extracorporeal blood circuit of a patient and identifying a needle dislodgement, comprises: identifying a potential needle dislodgement event based on changes in an arterial pressure and/or a venous pressure of the extracorporeal blood circuit; identifying an arterial heart rate of the patient by analyzing changes in an arterial pressure of the extracorporeal blood circuit; searching for a venous heart rate of a patient by analyzing changes in the venous pressure of the extracorporeal blood circuit, wherein the searching is enhanced based on the identified arterial heart rate; and verifying the potential needle dislodgement event is a needle dislodgement based on the absence of the venous heart rate.

Alternatively or additionally to any of the examples above, analyzing changes in venous pressure can include utilizing a lock-in signal processing technique to filter the venous pressure data. Alternatively or additionally to any of the examples above, the venous heart rate of the patient is searched for using an algorithm that analyzes the venous pressure by: filtering data from a venous pressure signal to produce filtered pressure data (FPD); computing a peak to peak (PTP) value by subtracting a min FPD from a max FPD; computing a prominence value based on the PTP value; identifying and indexing peaks from the FPD with a prominence above a prominence threshold (PT) and a distance between each peak above a minimum peak distance (min PD); calculating peak times when more than one peak is indexed; and calculating the venous heart rate based on the peak times. Alternatively or additionally to any of the examples above, the method can further include verifying the potential needle dislodgement event is not a needle dislodgement based on the presence of the venous heart rate (HR) within a set venous HR range, a variance of the FPD within a set variance range, and a blood pump rate (BPR) within a set BPR range. Alternatively or additionally to any of the examples above, the set venous HR range can be determined based on the identified arterial heart rate. Alternatively or additionally to any of the examples above, verifying the potential needle dislodgement event is not a needle dislodgement can further be based on the presence of the arterial heart rate within a set arterial heart rate range.

BRIEF DESCRIPTION OF THE DRAWINGS

To easily identify the discussion of any element or act, the most significant digit or digits in a reference number refer to the figure number in which that element is first introduced.

FIG. 13A illustrates a front view of a hemodialysis machine, in accordance with embodiments(s) of the present disclosure.

FIG. 13B illustrates an enlarged view of the dotted box portion of FIG. 13A with an illustration of an arterial line and venous line flow path, in accordance with embodiment(s) of the present disclosure.

FIG. 14A illustrates a front view of an optical sensor holding a venous line section, in accordance with embodiment(s) of the present disclosure.

FIG. 14B illustrates an isometric view of the optical sensor and venous line section of FIG. 14A, in accordance with embodiment(s) of the present disclosure.

FIG. 14C illustrates a cross-sectional view of the optical sensor of FIGS. 14A and 14B, in accordance with embodiment(s) of the present disclosure.

DETAILED DESCRIPTION

The foregoing has broadly outlined the features and technical advantages of the present disclosure such that the following detailed description of the disclosure may be better understood. It is to be appreciated by those skilled in the art that the embodiments disclosed may be readily utilized as a basis for modifying or designing other structures for carrying out the same purposes of the present disclosure. The novel features of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

The devices and methods explained in the present disclosure involve the use of sensors (e.g., pressure and optical) to monitor extracorporeal blood circuits, detect and measure a heart rate of a patient, and detect a needle dislodgement.

Figure 1:
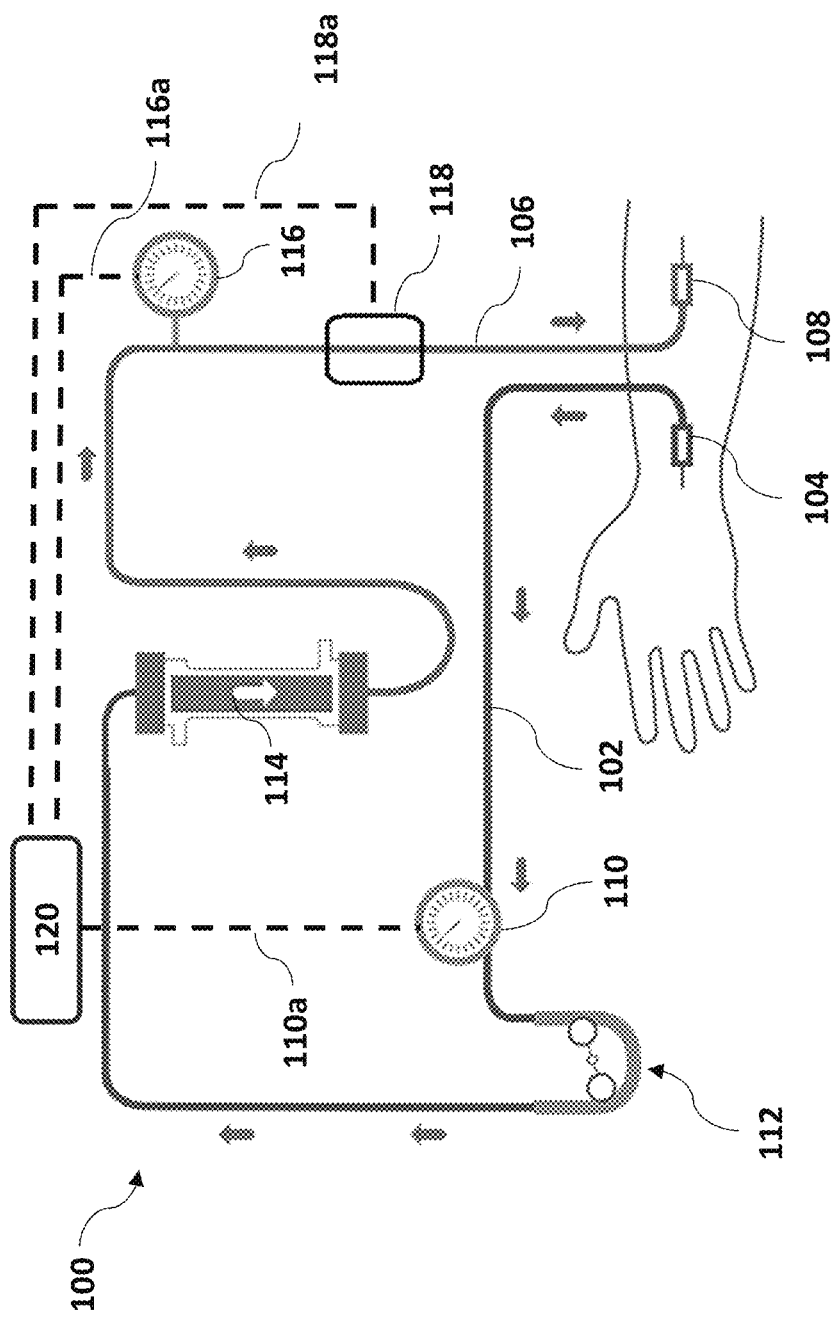
FIG. 1 illustrates a schematic of an extracorporeal blood circuit and needle dislodgement detection system, in accordance with embodiment(s) of the present disclosure.

FIG. 1 illustrates a schematic of an extracorporeal blood circuit 100, in accordance with non-limiting examples of the present disclosure. As shown in FIG. 1, blood may be drawn from an arm of a patient through an arterial line 102 connected to the patient via an arterial access 104 (e.g., needle, catheter, cannula). Blood may be returned to the patient after it is treated via a venous line 106 and a venous access 108 (e.g., needle, catheter, cannula). Extracorporeal blood circuit 100 may further include, among other things, an arterial pressure monitor 110, a blood pump 112, a blood treatment device 114, a venous pressure monitor 116, and an optical sensor 118. Tubing may be used for one or more sections (arterial line 102, venous line 106) of the extracorporeal blood circuit 100.

As shown in FIG. 1, arterial pressure monitor 110 may be connected to the arterial line 102 between arterial access 104 and blood pump 112, and configured to measure pressure of blood within arterial line 102 (i.e., arterial pressure) and transmit an arterial pressure signal 110a. Blood pump 112 may be configured to pump blood through extracorporeal blood circuit 100, including blood treatment device 114. The flow rate of blood through circuit 100 may be adjustable by increasing or decreasing the speed of blood pump 112. For example, the speed of blood pump may be controllable to produce a blood flow rate from 0 mL/min up to about 600 mL/min, or greater. Blood pump 112 may be, for example, a rotary pump or roller pump, or other suitable type pump. Blood treatment device 114 may take a variety of forms, including for example, a dialyzer that may be used for dialysis (e.g., hemodialysis). Venous pressure monitor 116 may be positioned along the venous line 106 between blood treatment device 114 and venous access 108, and configured to measure pressure of blood within venous line 106 (i.e., venous pressure) and transmit a venous pressure signal 116a.

Optical sensor 118 may be configured to releasably receive and/or couple to venous line 106, for example, between venous pressure monitor 116 and venous access 108. Optical sensor 118 may couple to the outside of venous line 106, which enables a non-invasive, air-free connection to venous line 106. Optical sensor 118 may be configured to transmit light energy at one or more wavelengths into venous line 106 and the blood flow. For example, optical sensor 118 may transmit light energy at RED wavelength, IR wavelength, green, blue wavelength, or other wavelengths. For example, optical sensor 118 may include one or more light sources (e.g., LEDs) and a first light source may output RED wavelength while a second light source may output IR wavelength. Optical sensor 118 may also detect backscattering of the transmitted light energy (e.g., RED, green, blue and/or IR), and generate an optical backscatter signal 118a. Optical backscatter signal 118a may include a single signal and/or multiple signals. For example, optical backscatter signal 118a may include a RED backscatter signal, an IR backscatter signal, green backscatter signal, blue backscatter signal, separate RED, IR, blue, and/or green backscatter signals, or a combined backscatter signal. A variety of optical sensors may be suitable, one example, includes MAX30102, which is available from Maxim Integrated Products, Inc.

Optical scattering from blood (pulsatile flow) in a tube can be detected using the optical sensor. The optical backscattering from the blood detected by the optical sensor can be a result of light scattering from a small region of blood near the tube inner surface, which can be based on the optical penetration depth. The flow profile of blood in the tube, the associated red blood cell concentration, and the red blood cell shape can change during each pulse of pulsatile blood flow in the tube of the extracorporeal blood circuit, and this can be detected by the optical back scattering by the optical sensor.

As shown in FIG. 1, a needle dislodgement detection system 120, may be configured to receive optical backscatter signal 118a from optical sensor 118, arterial pressure signal 110a, and venous pressure signal 116a.

Figure 2:
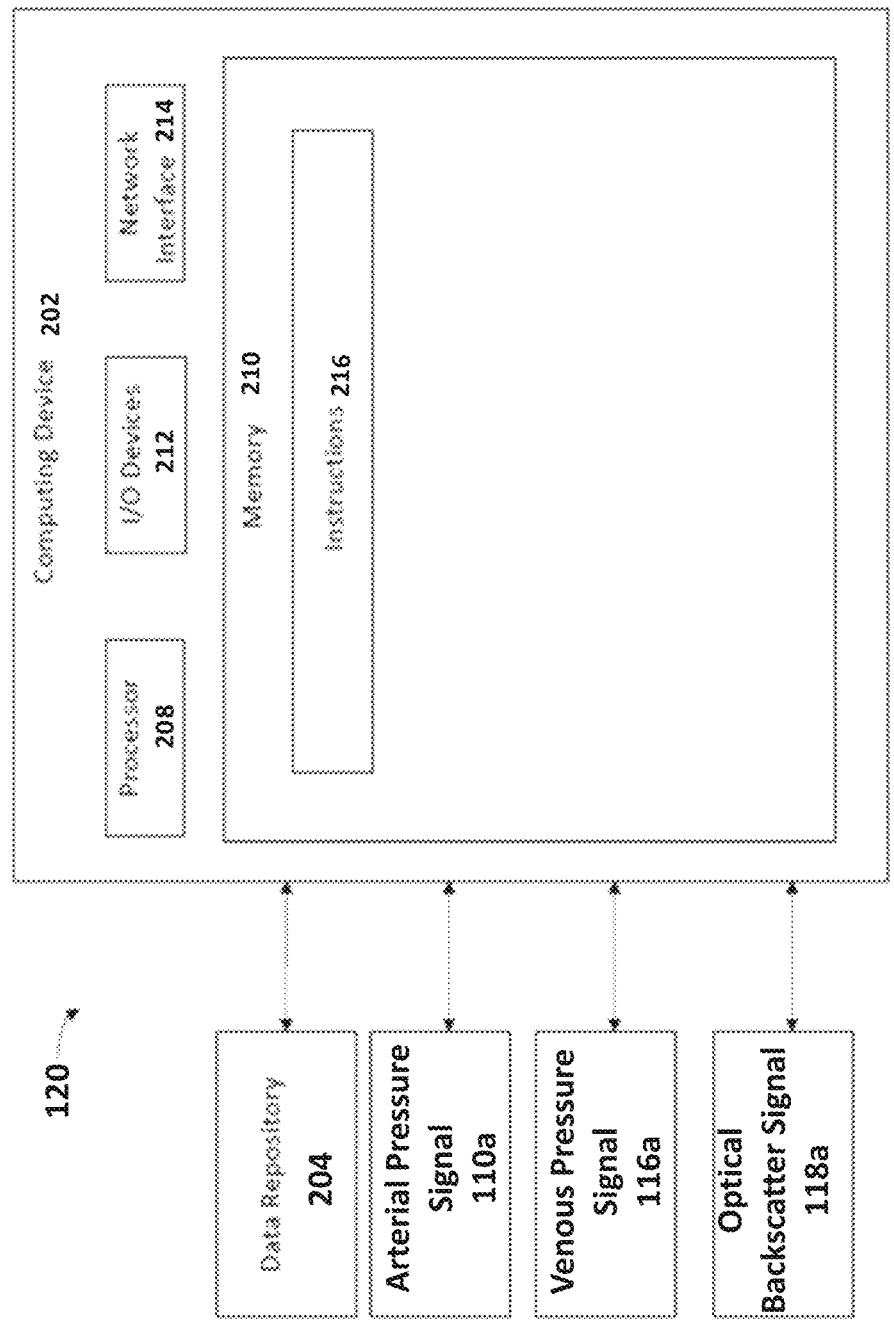
FIG. 2 illustrates a needle dislodgement detection system, in accordance with embodiment(s) of the present disclosure.

FIG. 2 illustrates a block diagram of needle dislodgement detection (NDD) system 120, in accordance with non-limiting examples of the present disclosure. NDD system 120 may include, among other things, a computing device 202 and a data repository 204.

The data repository 204 can represent one or more systems storing data that may be accessed and provided to the computing device 202 as further described herein. Although illustrated as separate from the computing device 202, some or all the components of the data repository 204 may be components of the computing device 202.

Computing device 202 may include, among other things, a processor 208, a memory 210, and I/O devices 212. Processor 208 may include circuitry or processor logic, such as, for example, any of a variety of commercial processors. In some examples, processor 208 may include multiple processors, a multi-threaded processor, a multi-core processor (whether the multiple cores coexist on the same or separate dies), and/or a multi-processor architecture of some other variety by which multiple physically separate processors are in some way linked. Additionally, in some examples, the processor 208 may include graphics processing portions and may include dedicated memory, multiple-threaded processing and/or some other parallel processing capability. In some examples, the processor 208 may be an application specific integrated circuit (ASIC) or a field programmable integrated circuit (FPGA).

Memory 210 may include logic, a portion of which includes arrays of integrated circuits, forming non-volatile memory to persistently store data or a combination of non-volatile memory and volatile memory. It is to be appreciated, that the memory 210 may be based on any of a variety of technologies. In particular, the arrays of integrated circuits included in memory 210 may be arranged to form one or more types of memory, such as, for example, dynamic random access memory (DRAM), NAND memory, NOR memory, or the like.

I/O devices 212 can be any of a variety of devices to receive input and/or provide output. For example, I/O devices 212 can include, a keyboard or keypad, a display (e.g., touch, non-touch, or the like), an LED, or the like.

Network interface 214 can include logic and/or features to support a communication interface. For example, network interface 214 may include one or more interfaces that operate according to various communication protocols or standards to communicate over direct or network communication links. Direct communications may occur via use of communication protocols or standards described in one or more industry standards (including progenies and variants). For example, network interface 214 may facilitate communication over a bus, such as, for example, peripheral component interconnect express (PCIe), non-volatile memory express (NVMe), universal serial bus (USB), system management bus (SMBus), SAS (e.g., serial attached small computer system interface (SCSI)) interfaces, serial AT attachment (SATA) interfaces, or the like. Additionally, network interface 214 can include logic and/or features to enable communication over a variety of wired or wireless network standards (e.g., 802.11 communication standards). For example, network interface 214 may be arranged to support wired communication protocols or standards, such as, Ethernet, RS-232, or the like. As another example, network interface 214 may be arranged to support wireless communication protocols or standards, such as, for example, Wi-Fi, Bluetooth, ZigBee, LTE, 5G, or the like.

Memory 210 can include instructions 216. During operation, processor 208 can execute instructions 216 to cause the computing device 202 to access data from the repository 204, for example, current and/or historical data for optical backscatter signal 118*a*, arterial pressure signal 110*a*, and venous pressure signal 116*a*, each of which may reside in records within one or more data repositories 104 or kept within memory 210. Instructions can include the various methods and processes (e.g., process 300, 400, 500, 600, 700, 900, 1000, 1100, 1200) discussed further herein.

Figure 3:
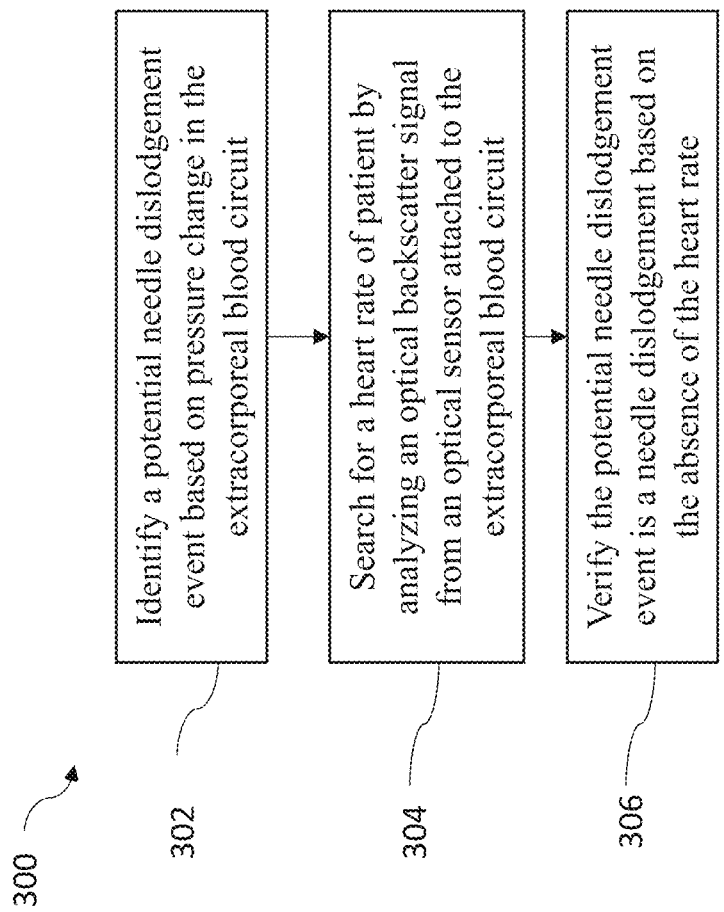
FIG. 3 illustrates a process for detecting a needle dislodgement of an extracorporeal blood circuit, in accordance with embodiments(s) of the present disclosure.
Figure 5:
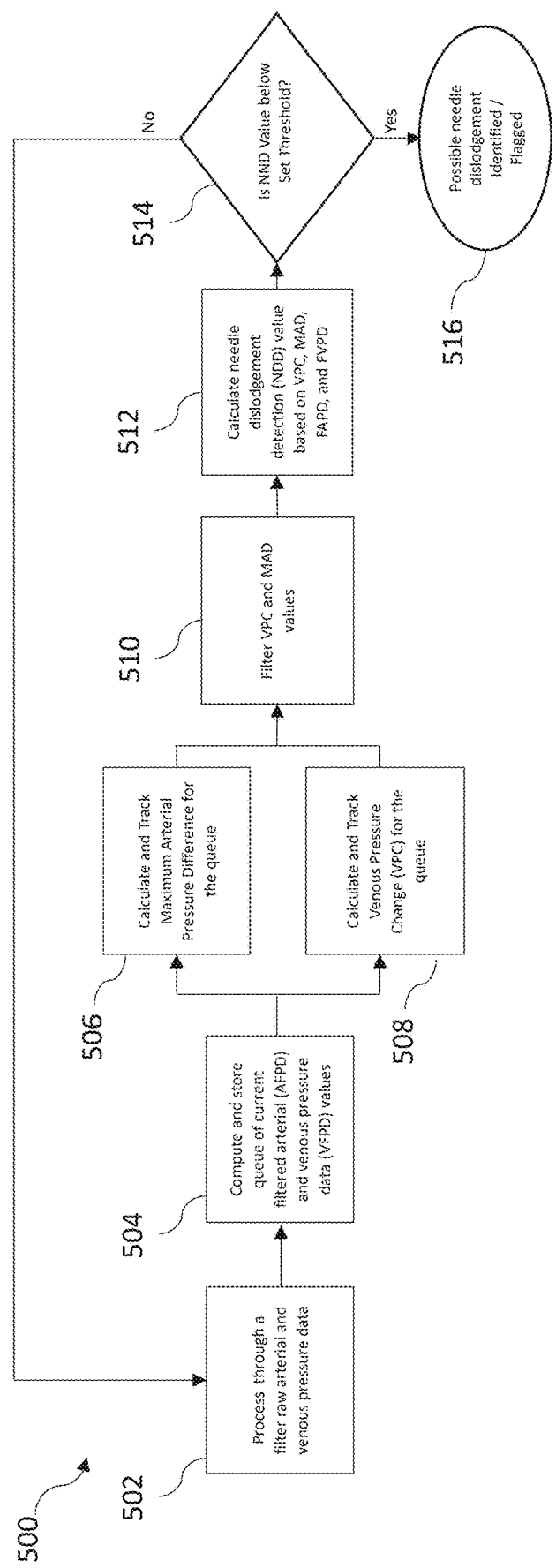
FIG. 5 illustrates a process for identifying a potential needle dislodgement event based on pressure in the extracorporeal blood circuit, in accordance with embodiments(s) of the present disclosure.

The process 300 of FIG. 3 shows steps for monitoring an extracorporeal blood circuit of a patient (e.g., circuit 100) and identifying a needle dislodgement, according to some implementations of the present disclosure. Process 300 may be performed, for example, by NDD system 120, or other devices and systems (e.g, dialysis system 1300 of FIG. 13) described herein. At step 302, process 300 can identify a potential needle dislodgement event based on pressure change (e.g., arterial and/or venous pressure) in the extracorporeal blood circuit. There are different techniques that may used to identify a potential needle dislodgement event based on pressure change. Process 500 described further herein in reference to FIG. 5, is one example of how step 302 may be performed.

Process 300, at step 304 can check for a heart rate of a patient by analyzing an optical backscatter signal (e.g., 118*a*) from an optical sensor (e.g., optical sensor 18) attached to extracorporeal blood circuit 100. Process 600 and Process 700 are described further herein in reference to FIGS. 6 and 7, and are examples of how step 304 may be performed.

Process 300, at step 306, can verify the potential needle dislodgement event is an actual needle dislodgement based on the absence of the heart rate. For example, if no heart rate is identified (e.g., by step 304) then the potential needle dislodgement can be verified as an actual needle dislodgement. If a heart rate is identified, then the potential needle dislodgement can be verified as a false positive. In response to verification of a needle dislodgement, NDD system 120 may initiate appropriate actions and alarms, alternatively, in response to verification of a false positive, NDD system 120 may clear or reset the potential needle dislodgement alarm (e.g., triggered by step 302).

Figure 4:
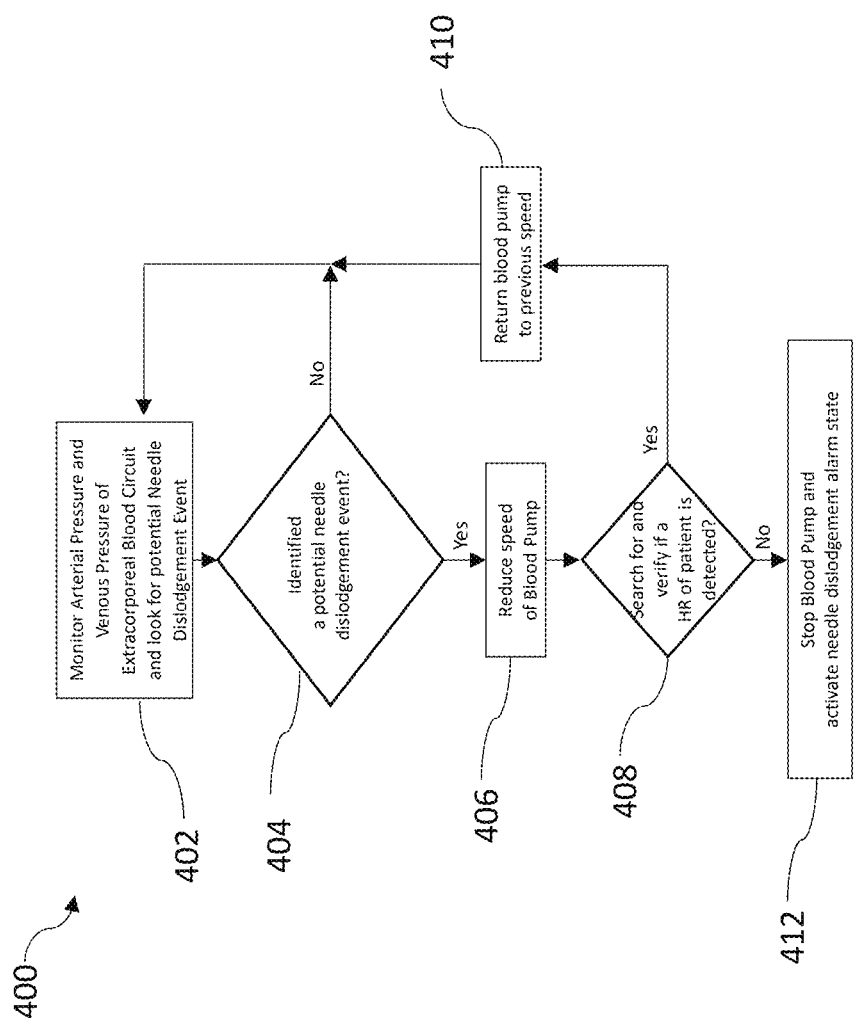
FIG. 4 illustrates a process for detecting a needle dislodgement of an extracorporeal blood circuit, in accordance with embodiments(s) of the present disclosure.

Process 400 of FIG. 4 shows steps for monitoring an extracorporeal blood circuit of a patient (e.g., circuit 100) and identifying a needle dislodgement, according to some implementations of the present disclosure. Process 400 may be performed, for example, by NDD system 120, or other devices and systems described herein. Process 400 may include some of the same steps as process 300, while also including some different and/or additional steps. At step 402 of process 400, the pressure (e.g., the arterial pressure and/or venous pressure) of the extracorporeal blood circuit may be monitored. For example, arterial pressure signal 110*a* and venous pressure signal 116*a* may be received and analyzed to search for a potential needle dislodgement event. At step 404, process 400 can check if a potential needle dislodgement has been identified. At step 404, if a potential needle dislodgement has not been identified (i.e., step 404, "No"), then process 400 can return to step 402 and process 400 can continue. At step 404, if a potential needle dislodgement has been identified (i.e., step 404, "Yes"), process 400 may proceed to step 406. Process 500 described further herein in reference to FIG. 5, is one example of a process that may be used to perform step 402 and/or step 404.

At step 406, the speed of the blood pump may be reduced. For example, the speed of blood pump may be reduced such that the blood flow rate is less than about 200 mL/min, about 150 mL/min, about 125 mL/min, about 100 mL/min, about 75 mL/min, or about 50 mL/min, or a speed between about 130-170 mL/min, about 150-200 mL/min, about 125-150 mL/min, about 100-125 mL/min, about 75-100 mL/min, about 50-75 mL/min, or about 50-120 mL/min. In some implementations, the speed of the blood pump may be reduced such that the flow rate drops to about 0 mL/min. The speed of the blood pump may be reduced rapidly, for example, in less than about 10 seconds, 5 seconds, 4 seconds, 3 seconds, 2 seconds, or 1 second. At step 408, the optical backscatter signal can be analyzed and used to search for and verify if a heart rate of the patient is detected. Process 600 and process 700 are described further herein in reference to FIGS. 6 and 7, and together are an example of how step 408 may be performed. At step 408, if a heart rate of the patient is detected (i.e., Step 408, "Yes"), then it can be confirmed that the identified potential needle dislodgement is a false alarm, and process 400 may proceed to step 410. At step 410, the blood pump speed can be increased in order to return the blood pump to its previous operating speed (e.g., speed prior to step 406), and then process 400 can return to step 402. At step 408, if a heart rate of the patient is not detected (i.e., Step 408, "No"), then it can be confirmed that the identified potential needle dislodgement is an actual needle dislodgement and process 400 can proceed to step 412. At step 412, process 400 can stop the blood pump and activate a needle dislodgement alarm state, and/or initiate other appropriate responsive action.

Process 500 of FIG. 5 shows the steps for identifying a potential needle dislodgement event based on pressure change in the extracorporeal blood circuit, according to some implementations of the present disclosure. For example, process 500 may be utilized to perform step 302 as shown in FIG. 3, steps 402/404 of FIG. 4, step 902 of FIG. 9, and/or steps 1002/1004 of FIG. 10. Process 500 may be performed, for example, by NDD system 120, or other devices and systems (see e.g., dialysis system 1300 of FIG. 13) described herein.

Identifying a needle dislodgement event based on pressure change can be challenging due to the variability in the pressure due to a number of factors. Blood loss caused by a needle dislodgement of the venous line will cause venous pressure to drop; however, other things may also cause the venous pressure to drop, for example, vertical movement of the patient's arm. Additionally, treatment conditions and other system components of a dialysis system may also impact pressure, including for example, the blood pump, ultrafiltration pump, substitution pump, and balance chamber.

Process 500, at step 502 can include processing, for example through a filter, raw arterial pressure data and venous pressure data received via arterial pressure signal 110a and venous pressure signal 116a. Processing may include filtering the raw data, for example, through a low pass filter to minimize the noise in the data. The processed pressure data values (e.g., PPD1, PPD2, PPD3, PPD ...) may be stored, for example, in data repository 204 and/or memory 210. The raw arterial and venous pressure data may be sampled at a frequency, for example, of once per second, 2 times per second, 5 times per second, 10 times per second, 20 times per second, 30 times per second, or greater.

Step 504 may include using the respective arterial and venous processed pressure data to compute and store a queue of current arterial filtered pressure data values and current venous filtered pressure data values. Current filtered pressure data (FPD) of each may be computed based on one or more previous PPD values (e.g., PPD1, PPD2, PPD3). For example, function 1 below may be used to calculate FPD:

$$FPD3 = PPD1 + PPD3 + 2*PPD2 - k_1*FPD1 + k_2*FPD2 \quad \text{Function 1}$$

Constant values $k_1$ and $k_2$ can be adjusted based on the desired level of smoothing. Function I can be executed and repeated for both arterial PPD and venous PPD values establishing a queue of current arterial filtered pressure data (AFPD) and a queue of current venous filtered pressure data (VFPD). The queue of current AFPD or VFPD values can include greater than 100 values, 150 values, 200 values, 250 values, or 300 values. For example, according to one implementation, a queue may include 280 AFPD values or 280 VFPD values corresponding to a duration of 14 seconds of data sampled at a rate of 20 times per second. Other sample rates and/or number of samples may be used for other implementations. Each queue of data (i.e., AFPD and VFPD) may be constantly updated as new data is received and new FPD values are computed thereby replacing the oldest data.

Step 506 can include calculating and storing a maximum arterial pressure difference (MAD), based on the maximum and minimum AFPD from the queue of AFPD. This may be calculated, for example, using function 2 below:

$$MAD = \text{Max } AFPD - \text{Minimum } AFPD \quad \text{Function 2}$$

Process 500, at step 508 can include calculating and tracking venous pressure change (VPC). VPC may be calculated based on the current VFPD and the average VFPD for the queue, for example, using function 3 below:

$$VPC = \text{Current } VFPD - \text{queue average } (VFPD) \quad \text{Function 3}$$

Process 500, at step 510 can optionally include filtering of VPC and MAD values. For example, VPC or MAD values that are above a certain threshold or a standard deviation from the moving average may be excluded. This can help filter out anomalies in the data that may cause false positives.

Process 500, at step 512 can include calculating a needle dislodgement detection (NDD) value, the NDD value may be calculated, for example, based on VPC, MAD, VFPD, and AFPD using function 4 below:

$$NDD \text{ value} = VPC + \left(MAD*\left(1 + \left(\frac{(\text{Venous } FPD3 - \text{Arterial } FPD3)}{500}\right)\right)\right) \quad \text{Function 4}$$

At step 514, the NDD value can be compared to a set threshold. If the NND value is below the set threshold (i.e., step 514, "Yes"), then process 500 may proceed to step 516 where a possible needle dislodgement is identified or flagged. Reaching step 516 and thereby identifying a possible needle dislodgement can trigger, for example, process 300 moving from step 302 to step 304, process 400 moving from step 404 to step 406, process 900 moving from step 902 to 904, and/or process 1000 moving from step 1004 to step 1006. If the NND value is above the set threshold (i.e., step 514, "No"), then process 500 can return to step 502 and process 500 can repeat.

Figure 6:
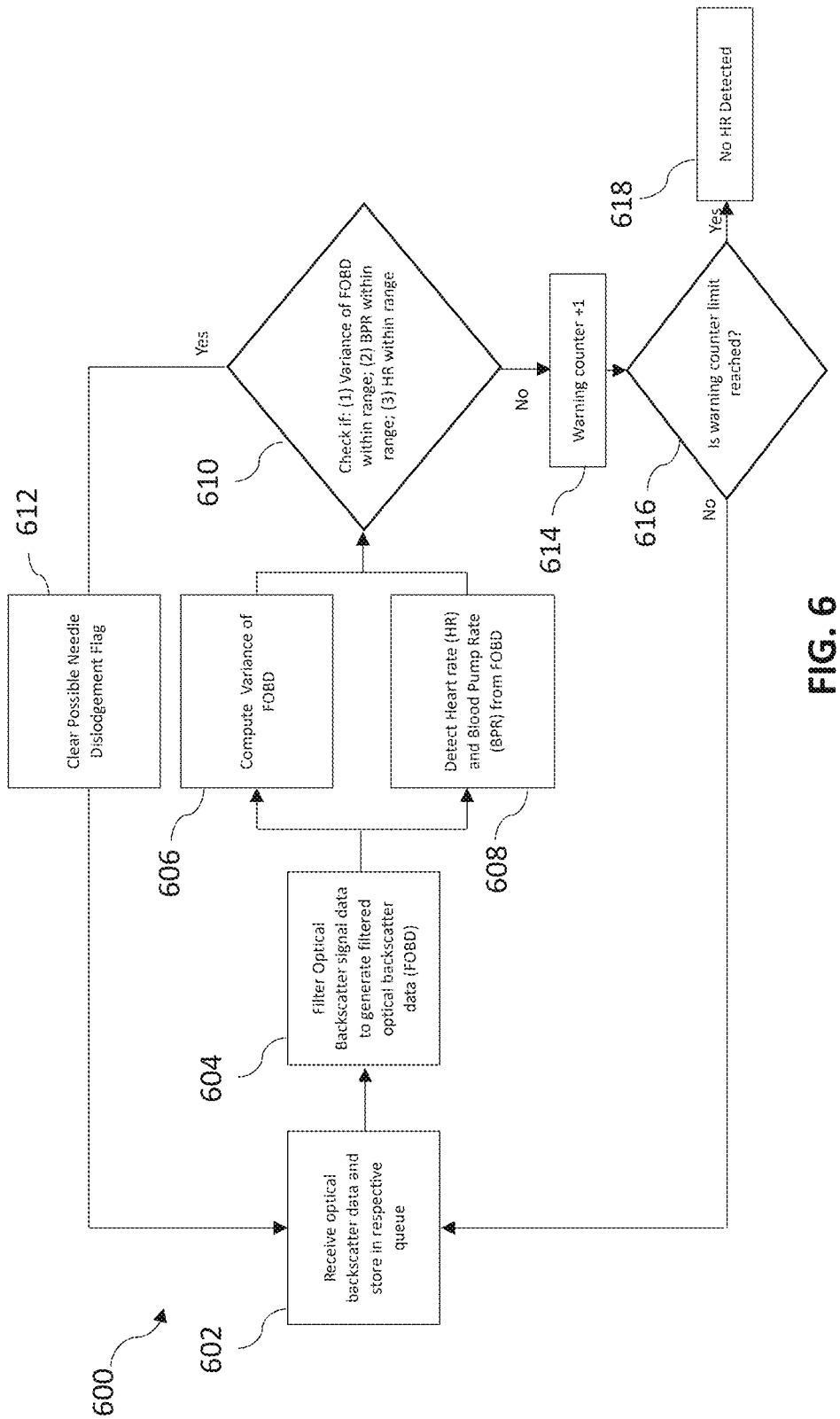
FIG. 6 illustrates a process for verifying a needle dislodgement based on absence of a heart rate detectable from an optical backscattering signal, in accordance with embodiments(s) of the present disclosure.

The process 600 of FIG. 6 shows steps that can be performed for verifying a needle dislodgement is an actual needle dislodgement based on the absence of the heart rate of a patient. For example, process 600 may be initiated by the completion of step 302 as shown in FIG. 3, and process 600 may be used to perform steps 304 and 306. Process 600 may also be initiated by the completion of step 406, as shown in FIG. 4, and process 600 may be used to perform step 408.

Process 600, at step 602 can include receiving the optical backscatter data and storing in a respective queue. The optical backscatter data may include multiple wavelengths of data, for example, red, IR, green, blue, all four of red, IR, green, and blue, and/or combination of two or more of the four. The optical backscatter data can be sampled at a frequency, for example, of at least 2 times per second, 5 times per second, 10 times per second, 20 times per second, 30 times per second, or greater.

Process 600, at step 604 can include filtering of the optical backscatter data stored in the queue to generate filtered optical backscatter data (FOBD). Filtering may include one or more smoothing, for example, sorting the optical backscatter data based on the smoothness of the data, for example, sorting into two categories (i.e., "smooth" or "slightly smooth") and then subtracting the smooth data from the slightly smooth data. In some embodiments, step 604 may include additional filtering and/or processing to generate FOBD, for example, this may include resampling at a higher rate, taking a first derivative of the data and/or taking a second derivative of the data. In some embodiments, step 604 may include a combination of steps, for example, resampling, smoothing, and taking a first derivative of the data and a second derivative of the data.

Process 600, at step 606 can include calculating a variance in the FOBD. Variance may be calculated, for example, by taking the average of squared deviations from the mean. Alternative techniques for calculating variance may also be utilized.

Process 600, at step 608 can include searching for and detecting, if present, a blood pump rate (BPR) and/or a heart rate (HR) of the patient from the FOBD. Process 700 of FIG. 7, for example, shows the steps that may be utilized to perform step 608, which will be described in further detail herein.

Process 600, at step 610 can include checking if the variance, BPR, and/or HR are within acceptable ranges. For example, if variance is less than a set threshold (e.g., a variance threshold), the BPR is within a set range (e.g., a BPR range), and the HR is within a set range (e.g., a HR range), these conditions may be used to verify there has not been a venous needle dislodgement (i.e., step 610, "Yes"), and process 600 may continue to step 612 and the possible needle dislodgement flag from step 516 of FIG. 5 can be cleared. Process 600 may return to step 602 or 604, following step 612. In some embodiments, at step 610, rather than looking at variance, BPR, and HR, step 610 may check just two or just one, of these three variables are within the respective set range. For example, in some embodiments step 610 may check the variance is within an acceptable variance range or below the variance threshold and check HR is present and/or within the set HR range. In another embodiment, step 610 may simply check if the HR is present and/or within a set HR range, and if so, then process 600 may proceed to step 612. In other embodiments, additional conditions may be checked in addition to variance, BPR, and HR. At step 610, if the variance, BPR, and/or HR are not within acceptable ranges (i.e., step 610, "No"), process 600 may proceed to step 614 at which a warning counter may be increased (e.g., +1), and then step 616 can check if the warning counter has reached a warning counter limit setpoint (e.g., 1, 2, 3, 4, 5, 6 . . . ). If the warning counter limit has not been reached (i.e., step 616, "No"), process 600 may return to step 602 or step 604, enabling process 600 to repeat. If the warning counter limit has been reached (i.e., step 616, "Yes"), process 600 may proceed to step 618 and confirm no heart rate of patient detected. In some embodiments, following a "No" at step 610, process 600 can proceed directly to step 618. Reaching step 618, can be used as the determination no HR has been detected and verification that the possible needle dislodgement is an actual needle dislodgement. For example, reaching step 618 may trigger completion of step 306, or process 400 proceeding from step 408 to step 412, as shown in FIG. 4.

Figure 7:
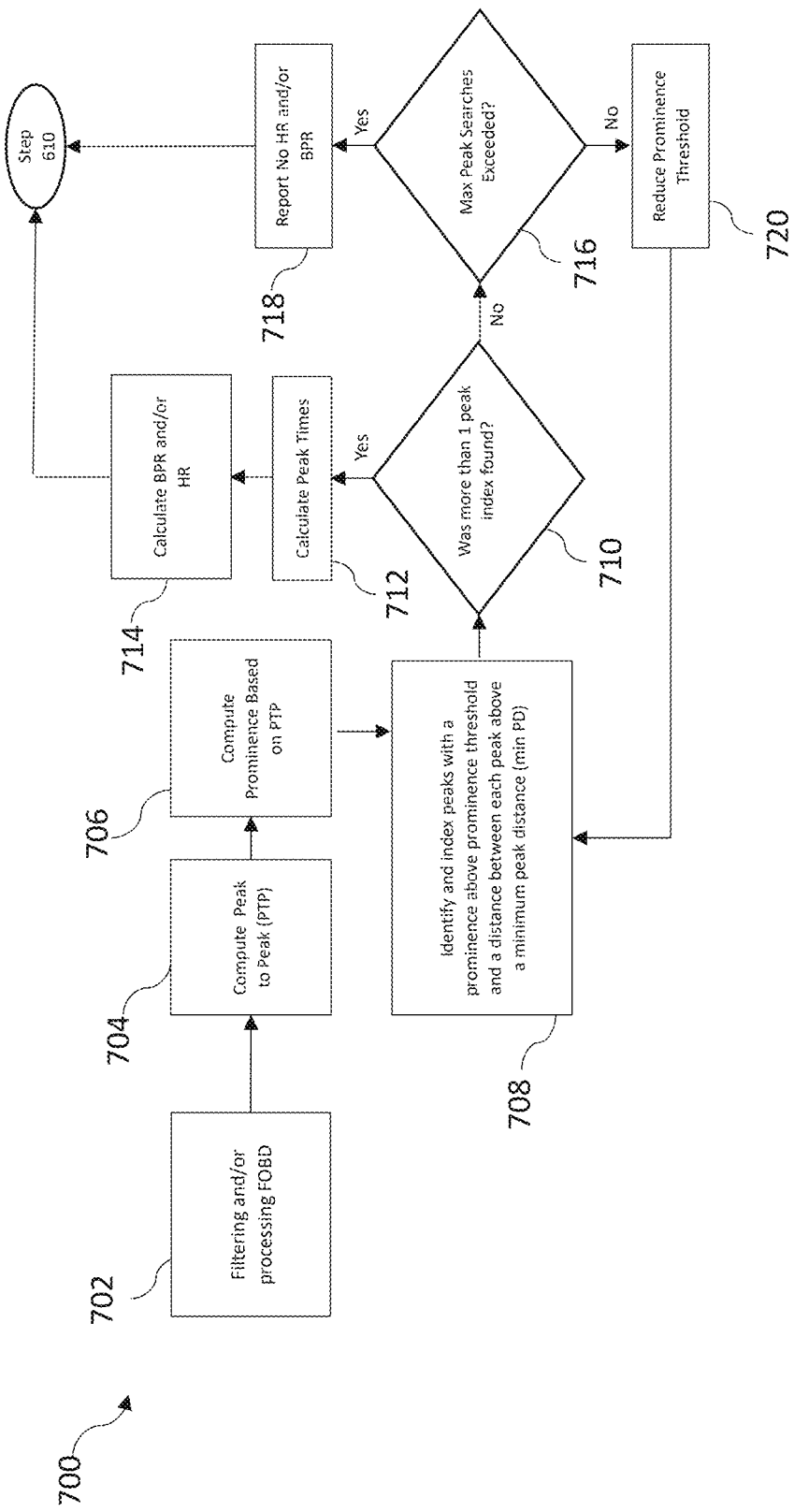
FIG. 7 illustrates a process for detecting a heart rate and/or a blood pump rate from an optical backscattering signal, which may be performed as part of the process of FIG. 6, in accordance with embodiments(s) of the present disclosure.

Now turning to process 700 of FIG. 7. The steps of process 700, as described herein can be performed to complete step 608 of process 600, according to some implementations. Other techniques or processes for carrying out step 608 may be implemented.

Process 700 may begin with step 702, which may optionally include additional filtering and/or processing of FOBD. For example, this may include dealing with non-number values (if present), removing DC offset, and/or applying a moving average to FOBD. In some embodiments, step 702 may include additional filtering and/or processing of the FOBD, for example, this may include resampling at a higher rate, taking a first derivative of the data and/or taking a second derivative of the data. In some embodiments, step 702 may include a combination of steps, for example, resampling, smoothing, and taking a first derivative of the data and a second derivative of the data.

The duration of FOBD in the queue being utilized for process 700 can be, for example, between about 0-5 seconds, 5-10 seconds, 5-15 seconds, 5-20 seconds, or 10-20 seconds. As new data is received and processed, this new data can replace the oldest FOBD in the queue.

Process 700, at step 704 can include computing a peak-to-peak value (PTP). For example, PTP can be calculated using function 5:

$$PTP = \max(FOBD) - \min(FOBD) \qquad \text{Function 5}$$

Process 700, at step 706 can include computing a prominence (PROM) value used for process 700. For example, PROM can be calculated using function 6:

$$PROM = 0.5 * PTP \qquad \text{Function 6}$$

Process 700, at step 708 can include computing and indexing peaks in the FOBD, if present. The indexed peaks can be filtered such that the peaks indexed have a PROM above a prominence threshold and a distance between peaks is above a minimum peak distance (PD MIN).

Process 700, at step 710 can check if more than one peak was indexed. If more than one peak was indexed (i.e., step 710, "Yes"), then process 700 can proceed to step 712 that can include calculating peak times.

Step 714 can calculate a blood pump rate (BPR) and/or heart rate (HR) based on the peak times. In some embodiments, after a plurality of peak times are identified, step 714 can include running a clustering algorithm on the peaks to select a refined set for calculating the BPR and/or HR. Step 714 can include associating the peaks with either blood pump rate or heart rate. For example, in some implementations, the two most prominent index peaks can be associated with the blood pump and the blood pump rate can be calculated based on the time between these two peaks. The other peaks (i.e., less prominent) can be associated with a patient's heartbeat and the patient's heart rate can be calculated based on these less prominent peaks. In some implementations, NDD system 120 may be configured to receive as an input the blood pump rate, for example, from the blood pump or associated machine (e.g., dialysis machine 1300), and the peaks associated with the BPR rate (e.g., "most prominent") can be confirmed or in some implementations can be identified by the BPR input.

Figure 8A:
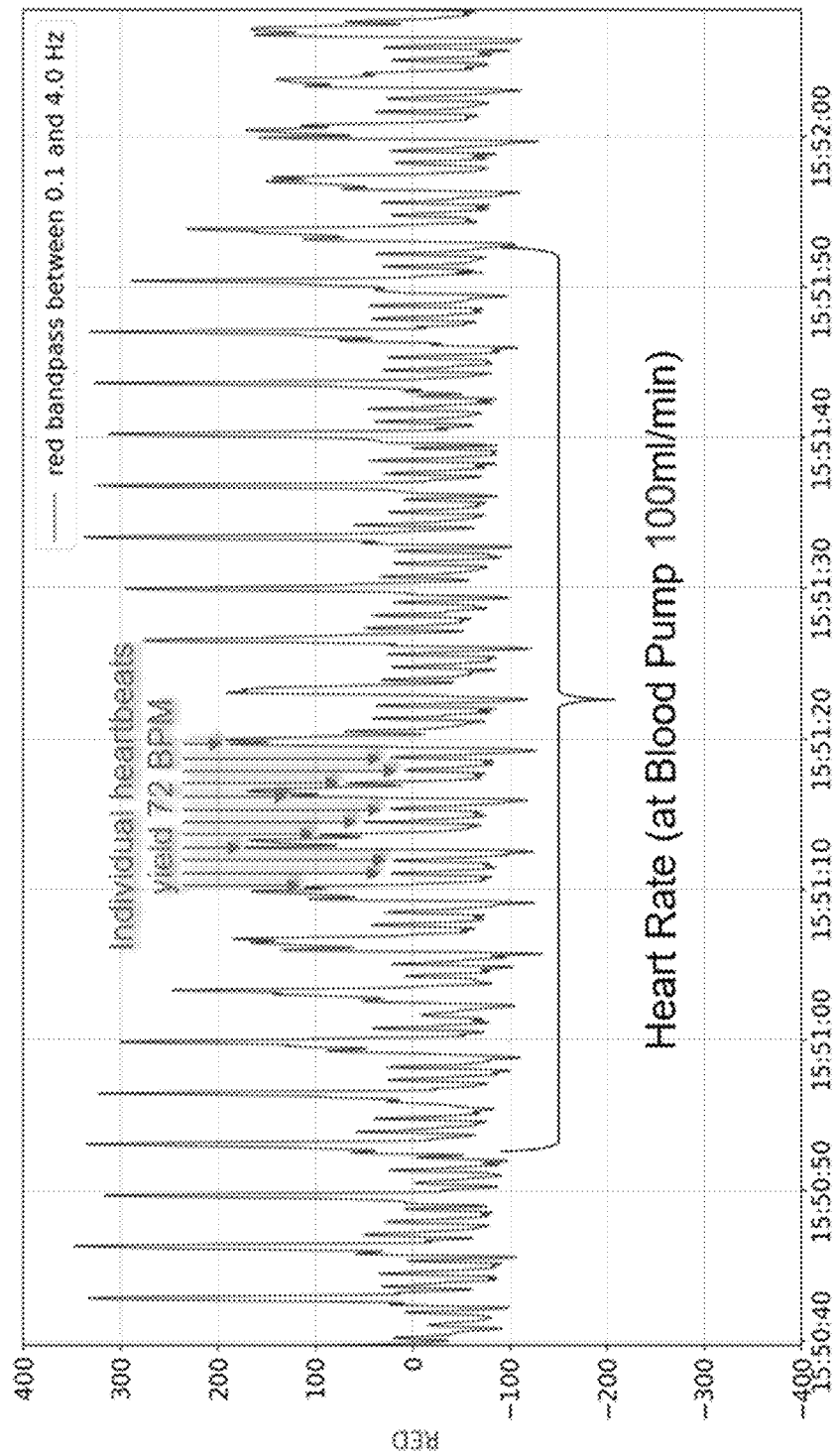
FIG. 8A is a plot of an optical backscatter signal vs time illustrating a detectable heart rate and blood pump rate, in accordance with embodiment(s) of the present disclosure.

The calculated BPR and/or HR can be used as the output from step 608 and input for Step 610, of process 600. FIG. 8A is a plot of FOPD vs. time illustrating a calculated BPR and HR, based on experimental lab data. As illustrated in FIG. 8, the blood pump was operated at a blood flow rate of 100 mL/min and a heart rate of 72 beats per minute was detected and calculated. For this experiment, a pump was utilized to simulate the heartbeat of a patient.

Figure 8B:
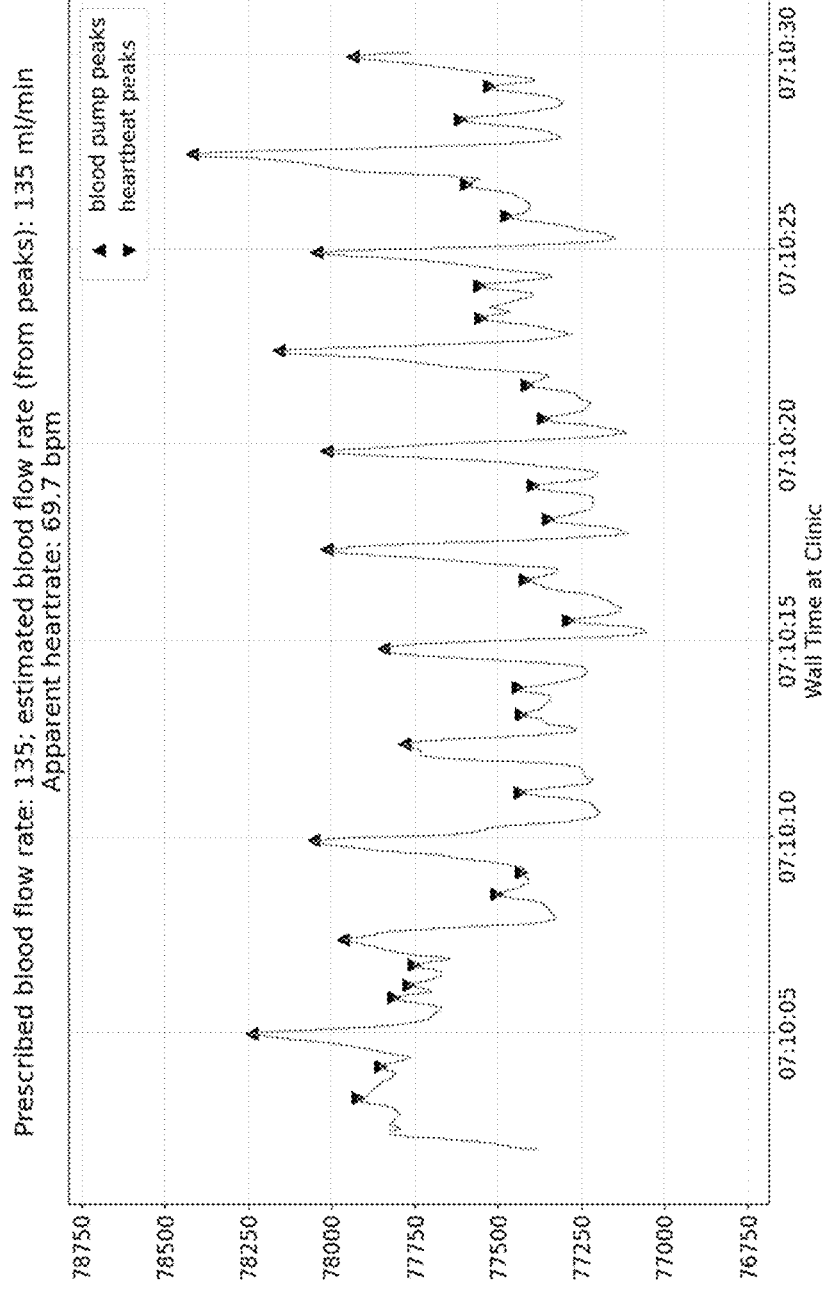
FIG. 8B is a plot of optical backscatter data vs time identifying heartbeat peaks and blood pump peaks from a clinical study visit (study visit 1), in accordance with embodiment(s) of the present disclosure.

FIG. 8B is a plot of FOPD vs. time illustrating identified blood pump peaks and heartbeat peaks, from which the blood pump rate (e.g., ~135 ml/min) and heart rate (e.g., ~69.7 bpm) can be calculated. The data used to plot FIG. 8B is from a clinical study visit (study visit 1), which is discussed further herein in reference to FIGS. 15A-15D.

At Step 710, if more than one peak is not indexed (i.e., step 710, "No"), then process 700 can proceed to step 716. At step 716, a check can be run to see if the maximum number of peak searches has been exceeded. If at Step 716, the maximum number of peaks searches has been exceeded (i.e., step 716, "Yes"), process 700 can proceed to step 718, which can report no HR and/or BPR was identified, which can be used at the output from step 608 for step 610, which would result in a "No" from step 610. At Step 716, if the maximum number of peak searches has not been exceeded (i.e., step 716, "No"), then process 700 can proceed to step 720, at which the prominence threshold utilized in step 708 can be reduced. Process 700 can then return to step 710 to be repeated with the reduced prominence threshold, thereby loosening the filter for indexed peaks.

In some implementations of process 700, rather than identifying and calculating BPR and/or HR based on a peak-to-peak calculation, a valley to valley calculation can be used to calculate BPR and/or HR. For example, this may be performed by inverting the FOBD (e.g., as part of the filtering and/or process of FOBD at step 702), thereby converting the valleys to peaks that can be utilized for steps 704-720. In some implementations, BPR can be calculated based on a peak-to-peak calculation while HR can be calculated based on valley to valley calculation. For example, process 700 can be performed using peak-to-peak to calculate BPR and then in parallel, process 700 can be run using valley to valley (i.e., by inverting FOBD at step 702) and HR can be calculated.

Figure 9:
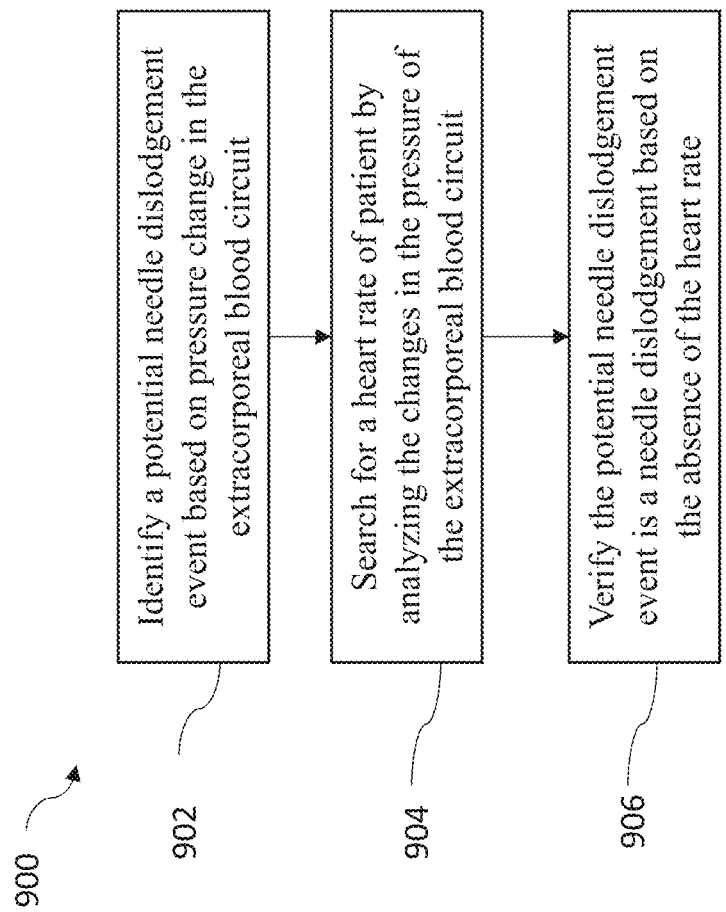
FIG. 9 illustrates a process for detecting a needle dislodgement of an extracorporeal blood circuit, in accordance with embodiments(s) of the present disclosure.
Figure 10:
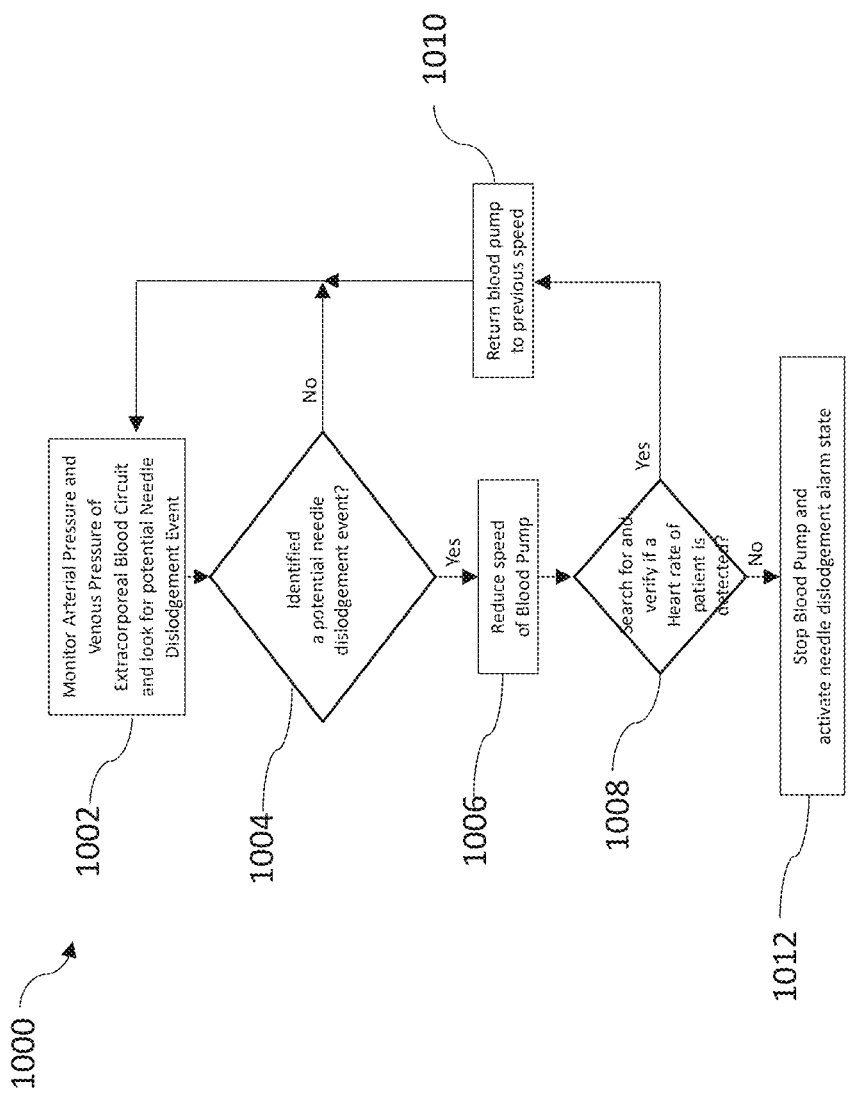
FIG. 10 illustrates a flow diagram for a dialysis system with needle dislodgement detection, in accordance with embodiments(s) of the present disclosure.

In contrast to process 300, in some implementations of the present disclosure, the pressure of the extracorporeal blood circuit can be used to identify and check for a heart rate of the patient and verify the needle dislodgement, instead of utilizing the optical backscatter signal. For example, the process 900 of FIG. 9 and process 1000 of FIG. 10 show processes for monitoring an extracorporeal blood circuit of a patient (e.g., circuit 100) and identifying a needle dislodgement based on analyzing the pressure change in the extracorporeal blood circuit. Process 900 may be performed, for example, by NDD system 120, or other devices and systems described herein. At step 902, process 900 can identify a potential needle dislodgement event based on pressure change (e.g., arterial and/or venous pressure) in the extracorporeal blood circuit. There are different techniques that may used to identify a potential needle dislodgement event based on process change. Process 500 described herein in reference to FIG. 5, is one example of how step 902 may be performed.

Process 900, at step 904 can search for a heart rate of a patient by analyzing the changes in the pressure (e.g., arterial and/or venous pressure) of the extracorporeal blood circuit 100. Process 1100 and Process 1200 described further herein in reference to FIGS. 11 and 12, are examples of how step 904 may be performed.

Process 900, at step 906, can verify the potential needle dislodgement event is an actual needle dislodgement based on the absence of the heart rate. For example, if no heart rate is identified (e.g., at step 904) then the potential needle dislodgement can be verified as an actual needle dislodgement. If a heart rate is identified, then the potential needle dislodgement can be verified as a false positive. In response to verification of a needle dislodgement, NDD system 120 may initiate appropriate actions and alarms, alternatively, in response to verification of a false positive, NDD system 120 may clear or reset the potential needle dislodgement alarm.

Now turning to process 1000 and FIG. 10, process 1000 may be performed, for example, by NDD system 120, or other devices and systems described herein. Process 1000 may include some of the same steps as process 900, while also including some different and/or additional steps. At step 1002, the pressure (e.g., the arterial pressure and/or venous pressure) of the extracorporeal blood circuit may be monitored. For example, arterial pressure signal 110a and/or venous pressure signal 116a may be monitored and analyzed to search for a potential needle dislodgement event. At step 1004, process 1000 can check if a potential needle dislodgement has been identified. At step 1004, if a potential needle dislodgement has not been identified (i.e., step 1004, "No"), then process 1000 can return to step 1002. At step 1004, if a potential needle dislodgement has been identified (i.e., step 1004, "Yes"), process 1000 may proceed to step 1006. Process 500 described herein in reference to FIG. 5, is one example of how steps 1002 and 1004 may be performed. At step 1006, the speed of the blood pump may be reduced. For example, the speed of blood pump may be reduced such that the flow rate is less than about 200 mL/min, about 150 mL/min, about 125 mL/min, about 100 mL/min, about 75 mL/min, or about 50 mL/min, or a speed between about 150-200 mL/min, about 125-150 mL/min, about 100-125 mL/min, about 75-100 mL/min, about 50-75 mL/min, or about 50-120 mL/min. In some implementations, the speed of the blood pump may be reduced such that the flow rate drops to zero mL/min. The speed of the blood pump may be reduced rapidly, for example, in less than about 5 seconds, 4 seconds, 3 seconds, 2 seconds, or 1 second. At step 1008, the pressure signal(s) (e.g., arterial pressure and/or venous pressure signal) of the extracorporeal blood circuit can be analyzed and used to search for and verify if a heart rate of the patient is detected. Process 1100 and process 1200 are described further herein in reference to FIGS. 11 and 12, and examples of how step 1008 may be performed. At step 1008, if a heart rate of the patient is detected (i.e., step 1008, "Yes"), then it can be confirmed that the identified potential needle dislodgement is a false alarm, and process 1000 may proceed to step 1010. At step 1010, the blood pump speed can be increased in order to return the blood pump to its previous operating speed (e.g., speed prior to step 1006), and then process 1000 can return to step 1002. At step 1008, if a heart rate of the patient is not detected (i.e., step 1008, "No"), then it can be confirmed that the identified potential needle dislodgement is an actual needle dislodgement and process 1000 can proceed to step 1012. At step 1012, process 1000 can stop the blood pump and activate a needle dislodgement alarm state, and/or take other appropriate responsive action.

Figure 11:
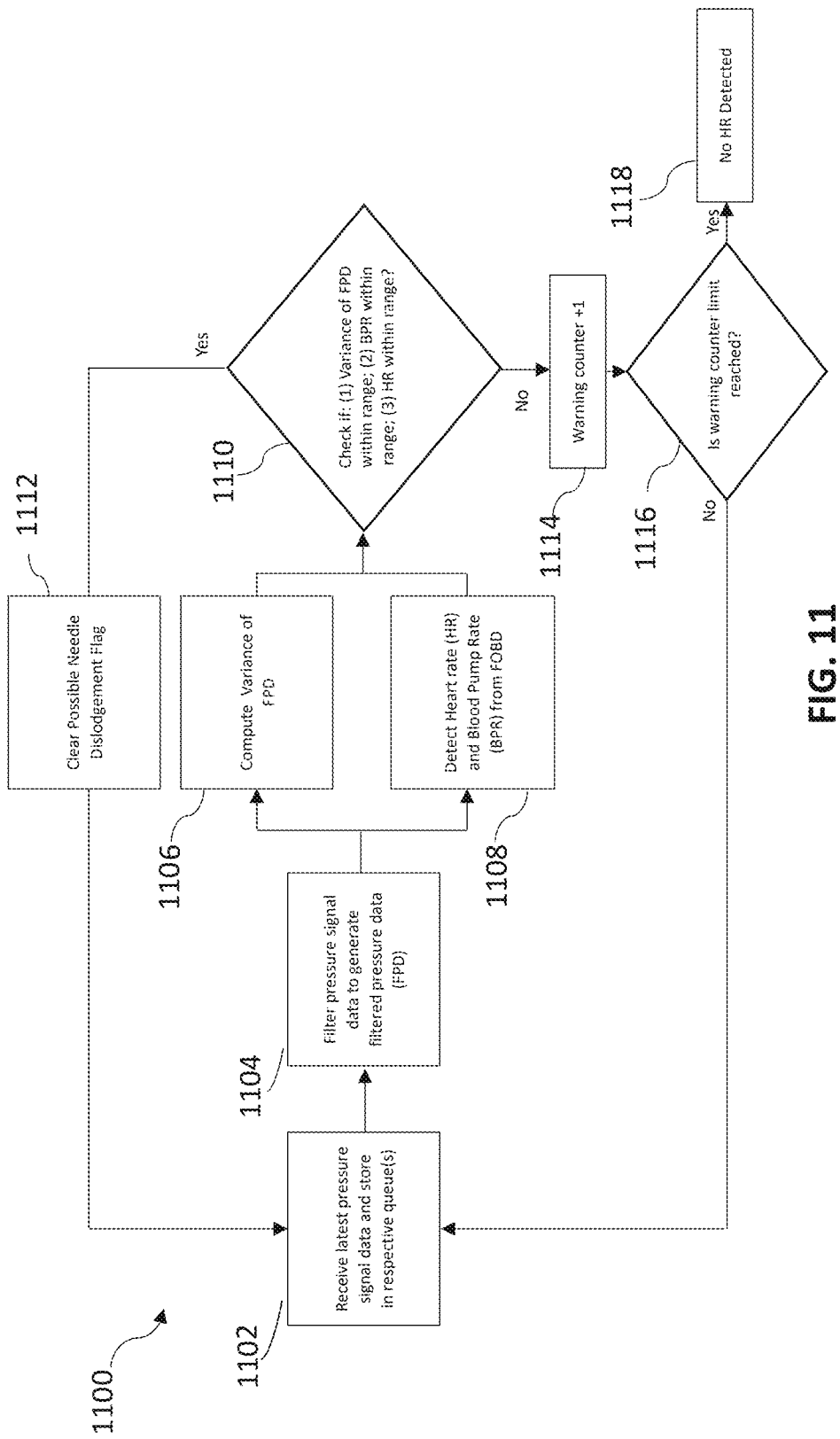
FIG. 11 illustrates a process for verifying a needle dislodgement based on absence of a heart rate detectable from pressure changes in the extracorporeal blood circuit, in accordance with embodiments(s) of the present disclosure.
Figure 12:
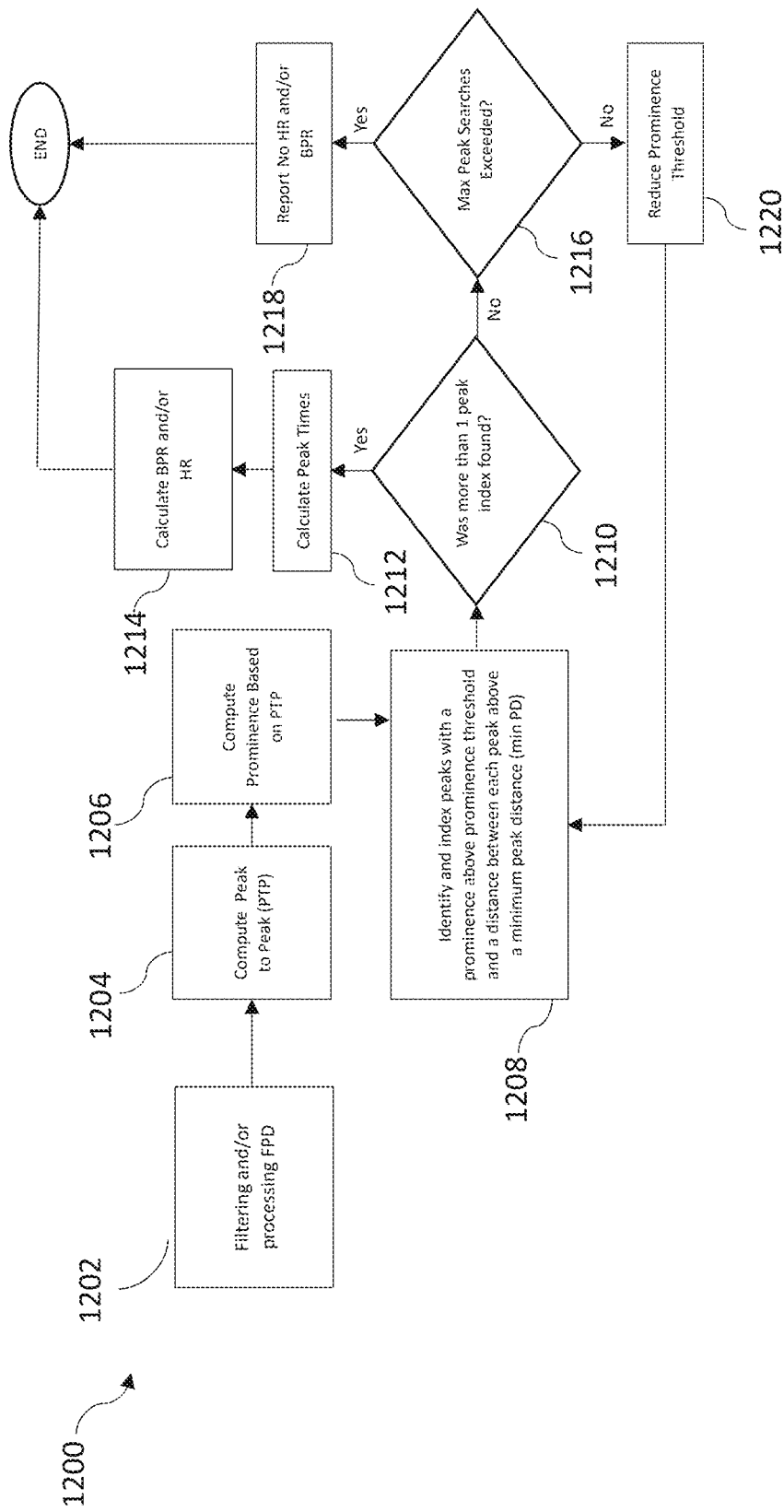
FIG. 12 illustrates a process for detecting a blood pump rate and/or heart rate from pressure changes in the extracorporeal blood circuit, which may be performed as part of the process of FIG. 11, in accordance with embodiments(s) of the present disclosure.

Process 1100 of FIG. 11 shows steps that can be performed for verifying a needle dislodgement is an actual needle dislodgement based on the absence of the heart of a patient. For example, process 1100 may be initiated by the completion of step 902 of process, and process 1100 may be used to perform steps 904 and 906, and/or process 1100 may be initiated by the completion of step 1006 and be used to perform step 1008.

Process 1100, at step 1102 can include receiving latest pressure signal data (e.g., arterial pressure signal 110a data and/or venous pressure signal 116a data) and storing it in a respective queue(s). The pressure signal data can be sampled at a frequency, for example, of at least 2 times per second, 5 times per second, 10 times per second, 20 times per second, 30 times per second, or greater.

Step 1104 can include filtering of the pressure signal data stored in the queue to generate filtered pressure signal data (FPD). In some implementations FPD can be just venous pressure data or in some implementations, FPD can utilize a combination of venous pressure data (VPD) and arterial pressure data (APD). For example, FPD values may be based on the following function 7 below.

$$FPD = scalefactor * APD - VPD \qquad \text{Function 7}$$

Filtering of the FPD may include, for example, sorting the pressure data based on the smoothness of the data, for example, sorting into two categories (i.e., "smooth" or "slightly smooth") and then subtracting the smooth data from the slightly smooth data. Step 1106 can include calculating a variance in the FPD. Variance may be calculated, for example, by taking the average of squared deviations from the mean. Alternative techniques for calculating variance may also be utilized. Step 1108 can include searching for and detecting, if present, a heart rate (HR) of the patient and/or a blood pump rate from the FPD. Process 1200 of FIG. 12 is one example of a process and the associated steps that may be performed to perform step 1108, which will be described in further detail herein.

Step 1110 can include checking if the variance, BPR, and/or HR are within acceptable ranges. For example, if variance is less than a set threshold (e.g., a variance threshold), the BPR is within a set range (e.g., a BPR range), and the HR is within a set range (e.g., a HR range), these conditions may be used to verify there has not been a venous needle dislodgement (i.e., step 1110, "Yes"), and process 1100 may continue to step 1112 and the possible needle dislodgement flag from step 516 of FIG. 5 can be cleared. Process 1100 may return to step 1102, following step 1112. In some implementations, rather than looking at variance, BPR, and HR, step 1110 may check for just two or just one of these three conditions. For example, in some embodiments step 1110 may check whether the variance is within an acceptable range and/or below the variance threshold and check HR is present and/or within the set HR range. In another embodiment, step 1110 may simply check if the HR is present and/or within the set range, and if so, then process 1100 may proceed to step 1112. In other embodiments, additional conditions may be checked in addition to variance, BPR, and HR. At step 1110, if the variance, BPR, and/or HR are not within acceptable ranges (i.e., step 1110, "No"), process 1100 may proceed to step 1114 at which a warning counter may be increased (e.g., +1), and then step 1116 can check if the warning counter has reached a warning counter limit setpoint (e.g., 1, 2, 3, 4, 5, 6 . . . ). If the warning counter limit has not been reached (i.e., step 1116, "No"), process 1100 may return to step 1102, enabling process 1100 to repeat. If the warning counter limit has been reached (i.e., step 1116, "Yes"), process 1100 may proceed to step 1118 and confirm no heart rate of patient detected. In some embodiments, following a "No" at step 1110, process 1100 can proceed directly to step 1116. Reaching step 1118 may be used as the trigger for completion of step 906 of process 900, as shown in FIG. 9 and/or trigger process 1000 proceeding from step 1008 to step 1012, as shown in FIG. 10.

Now turning to process 1200 of FIG. 12. The steps of process 1200, as described herein can be performed to complete step 1108 of process 1100, according to some implementations. Other techniques or processes for carrying out step 1108 may be implemented.

Process 1200 may begin with step 1202, which may optionally include additional filtering and processing of FPD. For example, this may include dealing with non-number values (if present), removing DC offset, and/or applying a moving average to FPD. The duration of FPD in the queue being utilized for process 1200 can be, for example, between about 0-5 seconds, 5-10 seconds, 5-15 seconds, 5-20 seconds, or 10-20 seconds. As new pressure data is received and processed, this new pressure data can replace the oldest FPD in the queue.

Process 1200, at step 1204 can include computing a peak-to-peak value (PTP). For example, PTP can be calculated using function 8:

$$PTP = \max(FPD) - \min(FPD) \qquad \text{Function 8}$$

Process 1200, at step 1206 can include computing a prominence (PROM) value used for process 1200. For example, PROM can be calculated using function 9:

$$PROM = 0.5 * PTP \qquad \text{Function 9}$$

Process 1200, at step 1208 can include computing and indexing peaks in the FPD, if present. The indexed peaks can be filtered such that the peaks indexed have a PROM above a prominence threshold and a distance between peaks is above a minimum peak distance (PD MIN).

Process 1200, at step 1210 can check if more than one peak was indexed. If more than one peak was indexed (i.e., step 1210, "Yes"), then process 1200 can proceed to step 1212 that can include calculating peak times. Step 1214 can calculate a blood pump rate (BPR) and/or heart rate (HR) based on the peak times. Step 1214 can include associating the peaks with either blood pump rate or heart rate. For example, in some implementations, the two most prominent indexed peaks can be associated with the blood pump and the blood pump rate can be calculated based on the time between these two peaks. The other peaks (i.e., less prominent) can be associated with a patient's heartbeat and the patient's heart rate can be calculated based on these less prominent peaks. In some implementations, NDD system 120 may be configured to receive as input the blood pump rate, for example, from the blood pump or associated machine (e.g., dialysis machine), and the peaks associated with the BPR rate (e.g., "most prominent") can be confirmed or in some implementations can be identified by the BPR input. The calculated BPR and/or HR can be used as the output from step 1108 and the check for Step 1110, of process 1100.

At Step 1210, if more than one peak was not indexed (i.e., step 1210, "No"), then process 1200 can proceed to step 1216. At step 1216, a check can be run to see if the maximum number of peak searches has been exceeded. If at Step 1216, the maximum number of peaks searches has been exceeded (i.e., step 1216, "Yes"), process 1200 can proceed to step 1218, which can report no HR and/or BPR was identified, which can be used at the output from step 1208. At Step 1216, if the maximum number of peak searches has not been exceeded (i.e., step 1216, "No"), then process 1200 can proceed to step 1220, at which the prominence threshold utilized in step 1208 can be reduced. Process 1200 can then return to step 1210 to be repeated with the reduced prominence threshold, thereby loosening the filter for indexed peaks.

In some implementations of process 1200, rather than identifying and calculating BPR and/or HR based on a peak-to-peak calculation, a valley-to-valley calculation can be used to calculate BPR and/or HR. For example, this may be performed by inverting the FPD (e.g., as part of the filtering and/or process of FPD at step 1202), thereby converting the valleys to peaks that can be utilized for steps 1204-1220. In some implementations, BPR can be calculated based on a peak-to-peak calculation while HR can be calculated based on valley-to-valley calculation. For example, process 1200 can be performed using peak to peak for calculating BPR and then in parallel, process 1200 can be run using valley to valley (i.e., by inverting FPD at step 1202) and HR can be calculated.

In some implementations of the present disclosure, process 300 and process 900 may be combined. For example, checking for a heart rate of the patient may be done by analyzing the changes in the pressure of the extracorporeal blood circuit and by analyzing the optical backscatter signal from the optical sensor attached to the extracorporeal blood circuit. Verifying the potential needle dislodgement is an actual needle dislodgement could be based on the absence of the heart rate from both processes 600/700 and process 1100/1200. Similarly, in some implementations, process 400 and process 1000 could be combined.

In some implementations of the present disclosure, the arterial pressure may be analyzed (e.g., via arterial pressure signal 110a) to identify a heart rate of the patient on the arterial line (e.g., an arterial heart rate). The pressure pulse generated by a patient's heart rate are usually more prominent in the arterial line than the venous line due to the arterial lines proximity to the vascular access of the patient. As a result, it can be easier to identify a patient's arterial heart rate. A variety of techniques may be implemented to analyze the arterial pressure signal 110a to identify the arterial heart rate. For example, process 1200 as described herein, may be utilized to identify the arterial heart rate by utilizing the arterial pressure signal data as the input data. A simplified version of process 1200 may also be utilized, for example, a process that identifies the peaks or valleys in the arterial pressure signal data and calculates the arterial heart rate based on the peak times.

In some implementations of the present disclosure, the identified arterial heart rate may be utilized to enhance the step of searching for the heart rate of the patient and/or the step of verifying the potential needle dislodgement event is a needle dislodgement based on an absence of the heart rate, of the various processes (e.g., 300, 400, 900, and/or 1000) described herein. According to one exemplary implementation, the arterial heart rate may be used to define the set HR range utilized in step 610 and/or step 1110. For example, the set HR range could be defined as plus or minus a number from the arterial heart rate. In some implementations, step 610 and/or step 1110 may include an additional check (i.e., (4)), for example, the presence of an arterial heart rate, an arterial heart within an expected range, and/or an arterial heart rate with a defined range of the HR (e.g., calculated by step 714 and/or step 1214).

According to another exemplary implementation, the arterial heart rate can be used to enhance the filtering and/or signal processing (e.g., to improve the signal to noise ratio) of the venous pressure signal and/or venous pressure signal data. For example, a lock-in amplifier or lock-in signal processing technique may be implemented wherein the identified arterial heart rate is utilized. This enhanced filtering and/or signal processing technique may be implemented, for example, as part of step 604 of process 600, step 702 of process 700, step 1104 of process 1100, and/or step 1202 of process 1200.

In some implementations, NDD system 120 as described herein may be integrated into a dialysis machine. For example, FIG. 13A shows a front view of a dialysis machine 1300. FIG. 13B shows an enlarged view of the dotted box portion of dialysis machine 1300 from FIG. 13A and an example flow path for the arterial and venous lines. In some implementations, the functionality and/or the hardware of NDD system 120 may be integrated with or may be part of dialysis machine 1300. For example, dialysis machine 1300 and its associated extracorporeal blood circuit 1301, may include, among other things, an arterial line 1302, an arterial pressure monitor 1310, a blood pump 1312, a venous line 1306, a venous pressure monitor 1316, and an optical sensor 1318. Dialysis machine 1300 may utilize a dialyzer (not shown), which may be connected in the flow path of the arterial and venous line as shown in FIG. 13B.

Optical sensor 118 as described herein can be integrated into a dialysis machine, for example, dialysis machine 1300 in the form of optical sensor 1318 or 1318', as shown in FIG. 13A and FIG. 13B. In some embodiments, optical sensor 1318 may be positioned below or downstream of the venous drip chamber 1320 and proximate to venous clamp 1322. In other embodiments, optical sensor 1318' may be positioned further downstream, closer to the patient's venous access. Positioning optical sensor 1318' further downstream may improve the performance by positioning optical sensor 1318' along portions of the venous line where the blood flow is predominantly laminar flow, for example, where the blood flow experiences less, limited, or about zero turbulent flow. In contrast, the portion of the venous line below the venous drip chamber 1320 and proximate the venous clamp 1322 may experience increased, greater or significant turbulent flow which may negatively impact the optical sensor 1318 performance and the optical backscattering signal. For example, the increased turbulent flow may increase the noise in the optical backscatter signal. Accordingly, optical sensor 118, 1318' may be positioned along a portion of the venous blood line that experiences predominately laminar flow, transitional or laminar flow, or not turbulent flow. For example, Reynolds numbers for blood flow in the venous line may be expressed as: greater than about 4000 is considered turbulent flow, about 2300-4000 is transitional flow, and less than about 2300 is laminar flow.

FIG. 14A shows a front view and FIG. 14B shows an isometric view of optical sensor 1318. Optical sensor 1318 may include a housing 1402 configured to receive venous line 1306. Optical sensor 1314 may further include a sensor door 1404 configured to close over and releasably secure venous line 1306. FIG. 14C shows a cross-sectional view of optical sensor 1318. As shown in FIG. 14C, optical sensor 1318 may include one or more light sources 1406 that are configured to direct the optical energy towards venous line 1306. Light sources 1406 may be part of a printed circuit board contained within housing 1402. Optical sensor 1318 may include a window 1408 positioned between light sources 1406 and venous line 1306 configured to allow passage of the optical energy and the optical backscattering. In some embodiments, the optical backscattering signal from optical sensor 1318 can be used to indicate whether door 1404 is properly closed based on the optical backscattering signal, and when it is identified that door 1404 is not closed, this can trigger an alarm or message to the operator to close and/or check the door of optical sensor 1318.

In some embodiments, optical sensor 118/1318 may also be used to sense blood within venous line 106/1306. For example, optical backscatter signal 110a may be monitored and used to identify when blood is present in the venous line. In some embodiments, analyzing optical backscatter signal 110 can enable estimating of the concentration of blood within the venous line. For example, the optical backscatter signal can be used to identify when the concentration of blood in the venous line is greater than about 10%, about 20%, about 30, about 40%, about 50%, about 60%, about 70% or higher, and/or alternatively less than about 70%, about 60%, about 50, about out 40%, about 30%, about 20%, about 10%, or lower.

In various implementations of the present disclosure, processes 300, 400, 500, 600, 700, 900, 1000, 1100, and/or 1200, described herein can be programmed instructions and/or one or programmed algorithms that may be stored in memory and run by a processor, which may be part of NDD system 120, computing device 202, dialysis machine 1300, and/or another controller/machine.

Some of the devices and processes described herein were tested in a study in a clinical setting. The study was conducted at a dialysis clinic during routine dialysis treatments of chronic hemodialysis patients who were dialyzed via an arteriovenous fistula or graft. The 2008T hemodialysis machines were utilized for the dialysis treatments, and an optical sensor (e.g., optical sensor 118) was connected to the venous blood line and optical backscatter data from the optical sensor was collected during the dialysis treatment. An FDA-approved pulse oximeter was connected to the subject's fingers on the non-vascular access side to serve as a reference device for continuous heart rate recording. During the study visits, the patients received their normal hemodialysis treatment according to their individual prescriptions, with the exception that the blood flow rate was temporarily reduced several times during the treatment for brief periods (about 30 seconds or less), after which the patient's prescribed blood flow rate was restored. The changes in the blood flow rate were implemented instantaneously rather than via a gradual ramp down by trained clinic staff per the approved protocol. This testing of reducing the blood flow rate was intended to mimic, for example, step 406 of process 400, which may be initiated in response to identification of a potential needle dislodgement event (e.g., Yes, at Step 404).

Figure 15A:
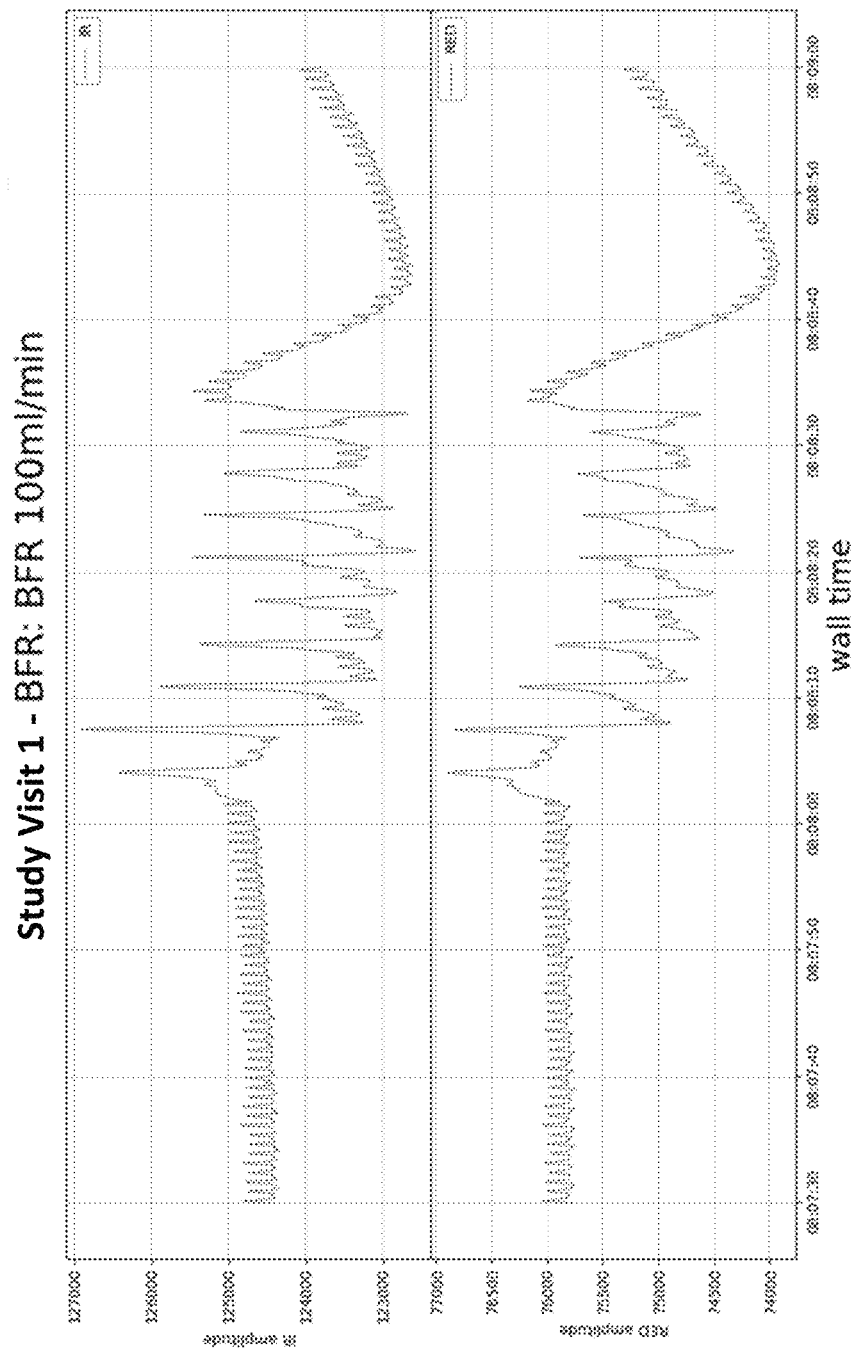
FIG. 15A is a plot of optical backscatter data vs time collected during study visit 1 of clinical testing during a period in which the blood flow rate was reduced from the patient's prescribed blood flow rate to 100 ml/min, in accordance with embodiment(s) of the present disclosure.
Figure 15B:
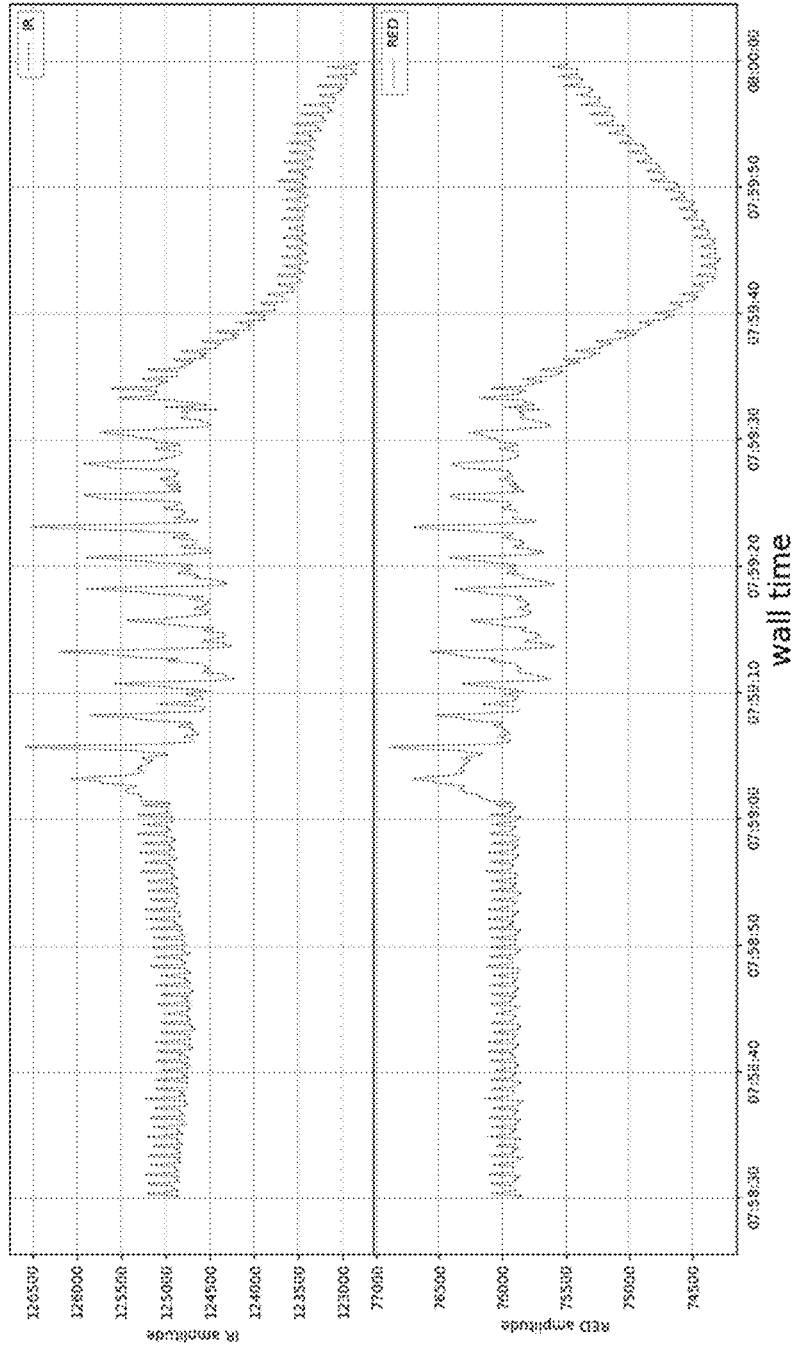
FIG. 15B is a plot of optical backscatter data vs time collected during study visit 1 of clinical testing during a period in which the blood flow rate was reduced from the patient's prescribed blood flow rate to 135 ml/min, in accordance with embodiment(s) of the present disclosure.
Figure 15C:
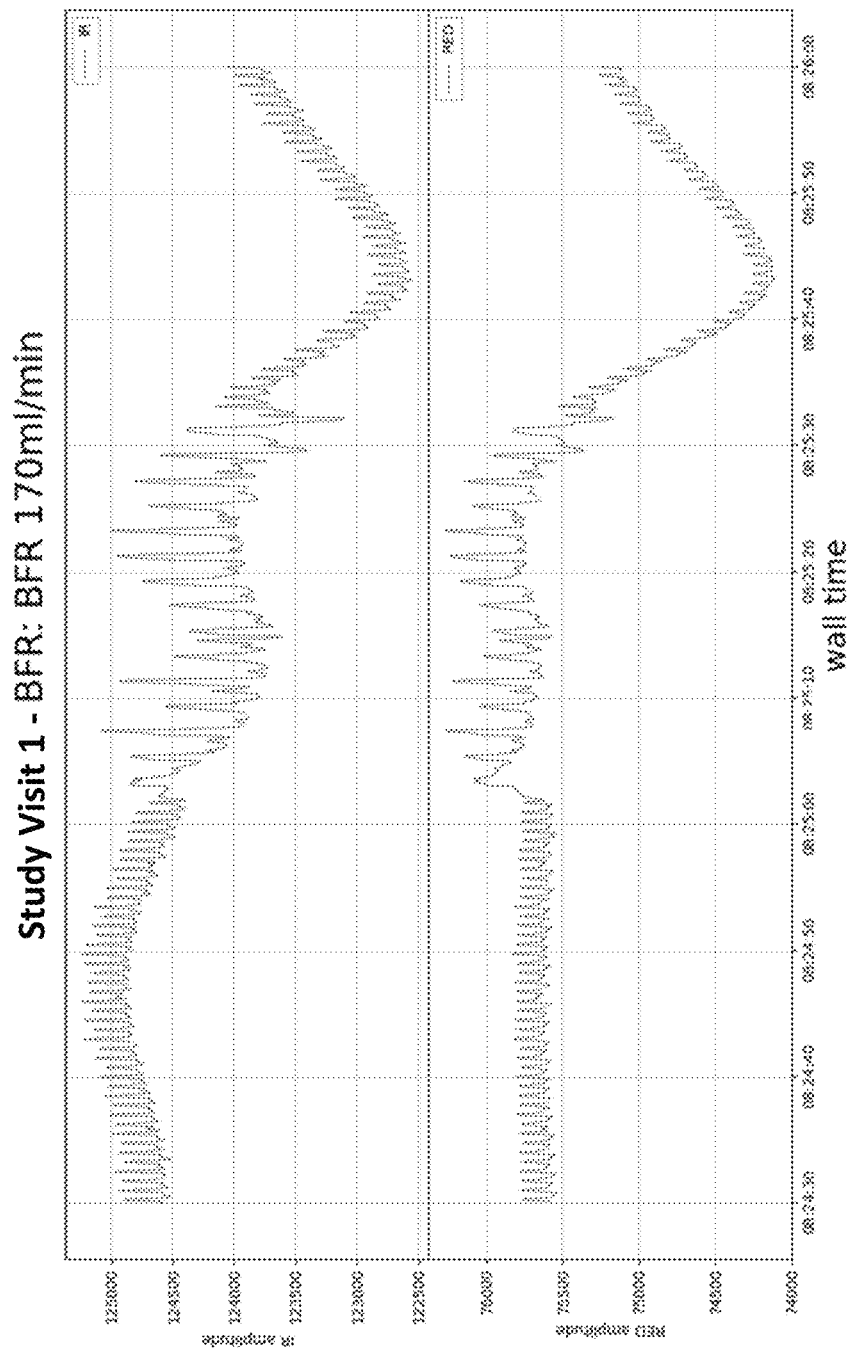
FIG. 15C is a plot of optical backscatter data vs time collected during study visit 1 of clinical testing during a period in which the blood flow rate was reduced from the patient's prescribed blood flow rate to 170 ml/min, in accordance with embodiment(s) of the present disclosure.
Figure 15D:
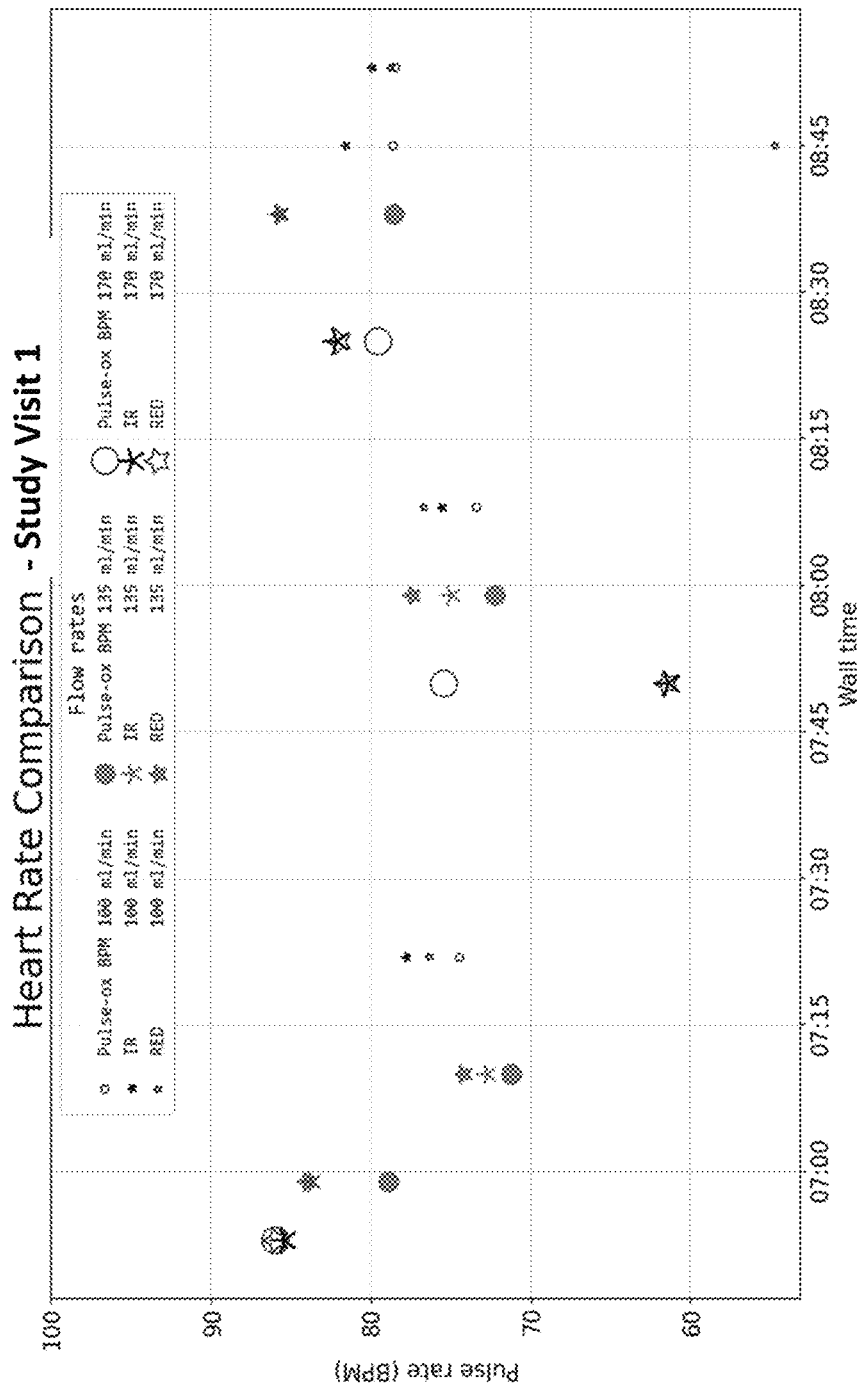
FIG. 15D is a plot of pulse rate versus time which includes the pulse rate of a pulse-ox and the pulse rate calculated based on the optical backscatter data from study visit 1, in accordance with embodiment(s) of the present disclosure.

FIG. 15A is a plot of a portion of the optical backscatter data (IR and Red) from one of the study visits (study visit 1), during a period when the blood flow rate was reduced from the patient's prescribed rate to 100 ml/min for about 30 seconds. FIG. 15B is a plot of another portion of the optical backscatter data (IR and Red) from study visit 1, during a period when the blood flow rate was reduced from the patient's prescribed rate to 135 ml/min. FIG. 15C is a plot of another portion of the optical backscatter data (IR and Red) from study visit 1, during a period when the blood flow rate was reduced from the patient's prescribed rate to 170 ml/min. The patient's prescribed blood flow rate for study visit 1 was 450 ml/min and the patient's access was an arteriovenous fistula. During study visit 1, the patient's prescribed blood flow rate was reduced a total 11 times, four times it was reduced to 100 ml/min, four times it was reduced to 135 ml/min, and 3 times it was reduced to 170 ml/min. The optical backscatter data during these periods of reduced blood flow rate was analyzed (e.g., utilizing process 700) to verify the presence and calculate a heart rate for the patient. FIG. 15D is a plot showing the identified and calculated heart rate (based on IR and Red backscatter date) for the patient during each of the periods of reduced blood flow rate along with the heart rate measured simultaneously by the pulse-ox.

Figure 16A:
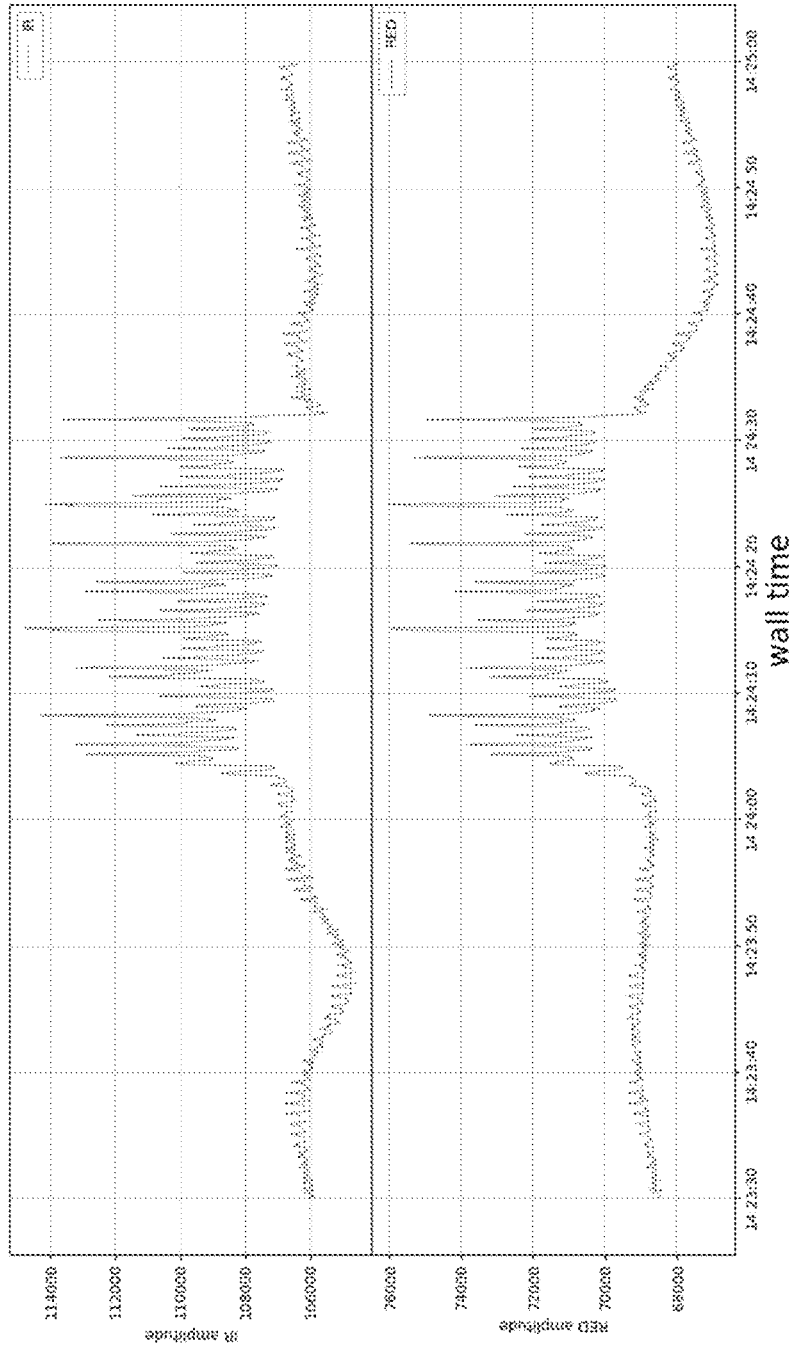
FIG. 16A is a plot of optical backscatter data vs time collected during study visit 2 of clinical testing during a period in which the blood flow rate was reduced from the patient's prescribed blood flow rate to 100 ml/min, in accordance with embodiment(s) of the present disclosure.
Figure 16B:
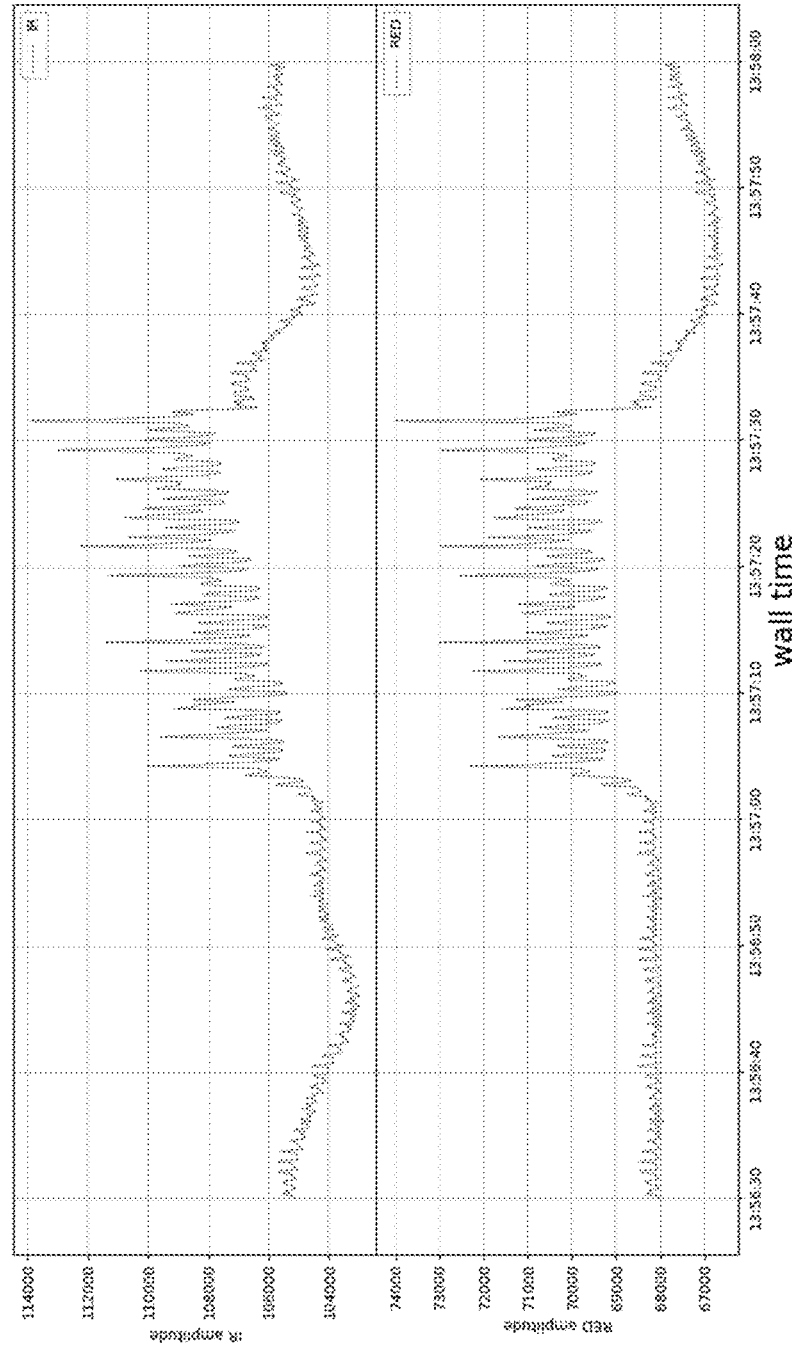
FIG. 16B is a plot of optical backscatter data vs time collected during study visit 2 of clinical testing during a period in which the blood flow rate was reduced from the patient's prescribed blood flow rate to 135 ml/min, in accordance with embodiment(s) of the present disclosure.
Figure 16C:
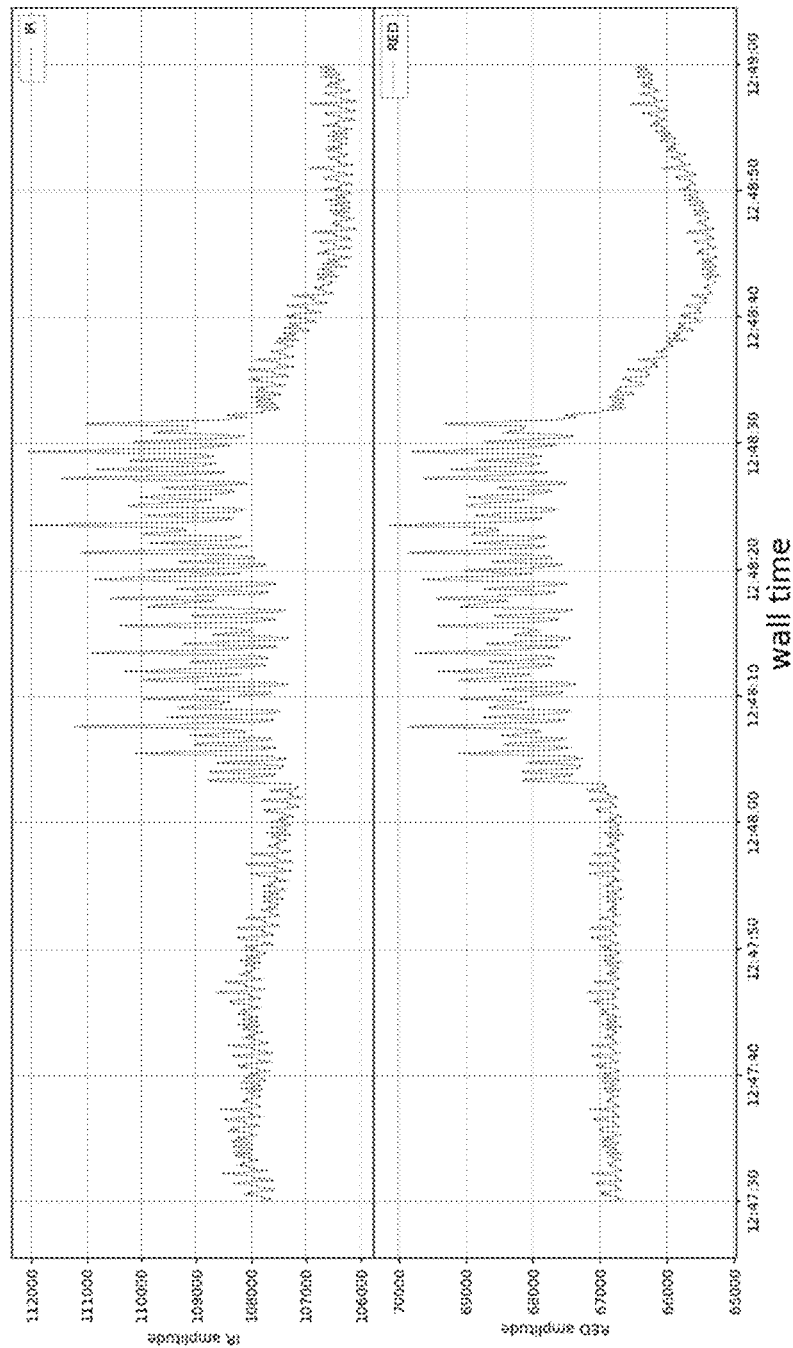
FIG. 16C is a plot of optical backscatter data vs time collected during study visit 2 of clinical testing during a period in which the blood flow rate was reduced from the patient's prescribed blood flow rate to 170 ml/min, in accordance with embodiment(s) of the present disclosure.
Figure 16D:
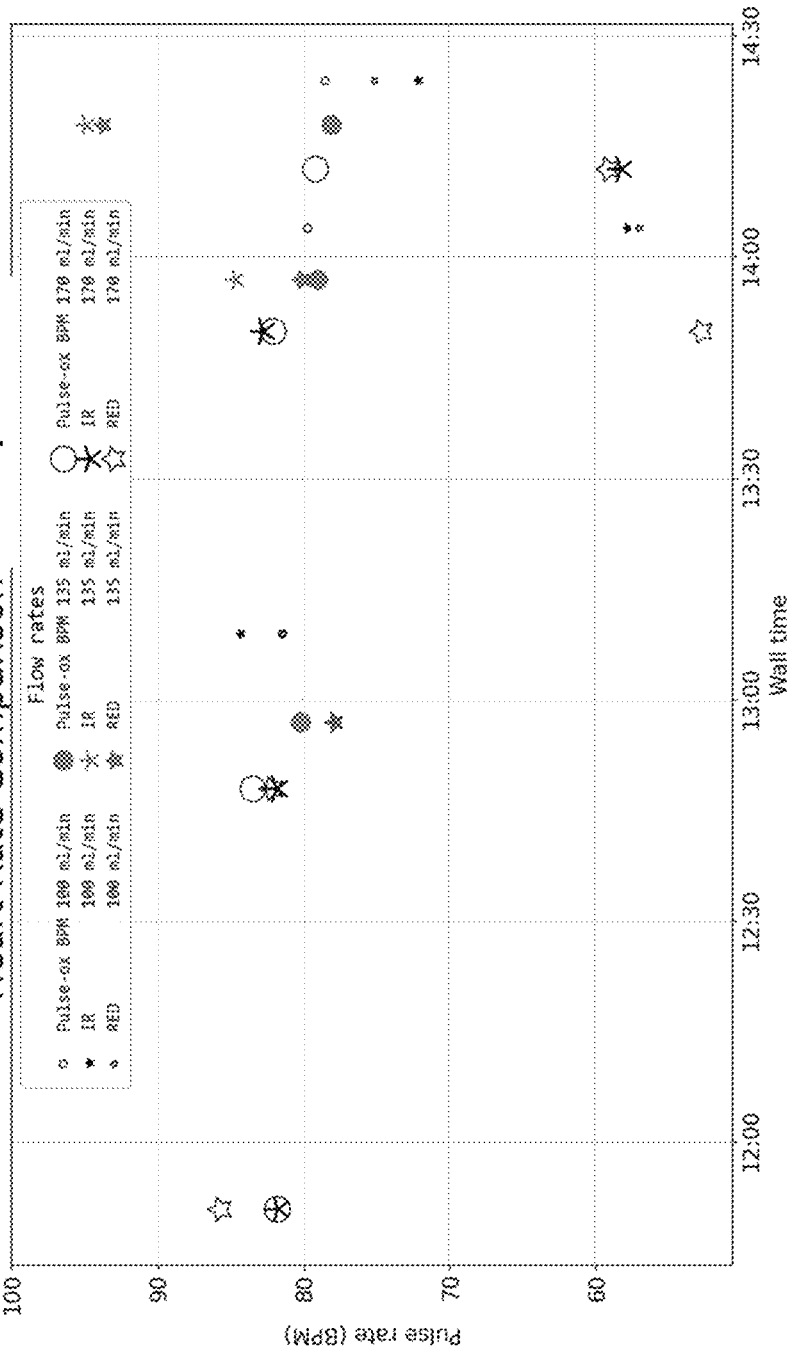
FIG. 16D is a plot of pulse rate versus time which includes the pulse rate of the pulse-ox and the pulse rate calculated based on the optical backscatter data from study visit 2, in accordance with embodiment(s) of the present disclosure.

FIG. 16A is a plot of a portion of the optical backscatter data (IR and Red) from another study visit (study visit 2), during a period when the blood flow rate was reduced from the patient's prescribed rate to 100 ml/min for about 30 seconds. FIG. 16B is a plot of another portion of the optical backscatter data (IR and Red) from the same study visit (study visit 2), during a period when the blood flow rate was reduced from the patient's prescribed rate to 135 ml/min. FIG. 16C is a plot of another portion of the optical backscatter data (IR and Red) from the same study visit, during a period when the blood flow rate was reduced from the patient's prescribed rate to 170 ml/min. The patient's prescribed blood flow rate for study visit 2 was 450 ml/min, but for a portion of the treatment it was reduced to 400 ml/min and the patient's access was a arteriovenous fistula. During study visit 2, the blood flow rate was reduced a total 10 times, 3 times it was reduced to 100 ml/min, 3 times it was reduced to 135 ml/min, and 4 times it was reduced to 170 ml/min. The optical backscatter data during these periods of reduced blood flow rate was then analyzed (e.g., utilizing process 700) to verify the presence and calculate a heart rate for the patient. FIG. 16D is a plot showing the calculated heart rate for the patient during each of these periods of reduced blood flow rate along with the heart rate measured simultaneously by the pulse-ox.

Figure 17A:
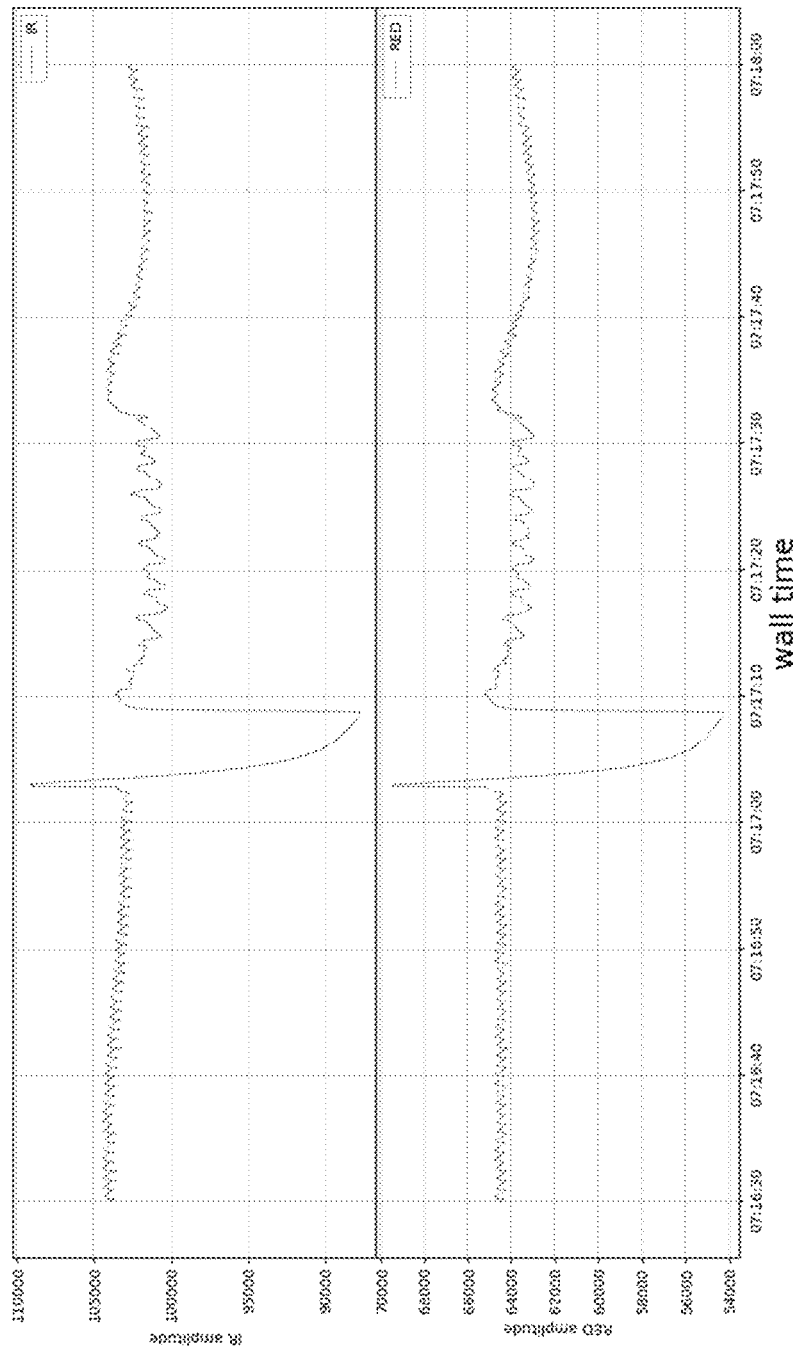
FIG. 17A is a plot of optical backscatter data vs time collected during study visit 3 of clinical testing during a period in which the blood flow rate was reduced from the patient's prescribed blood flow rate to 100 ml/min, in accordance with embodiment(s) of the present disclosure.
Figure 17B:
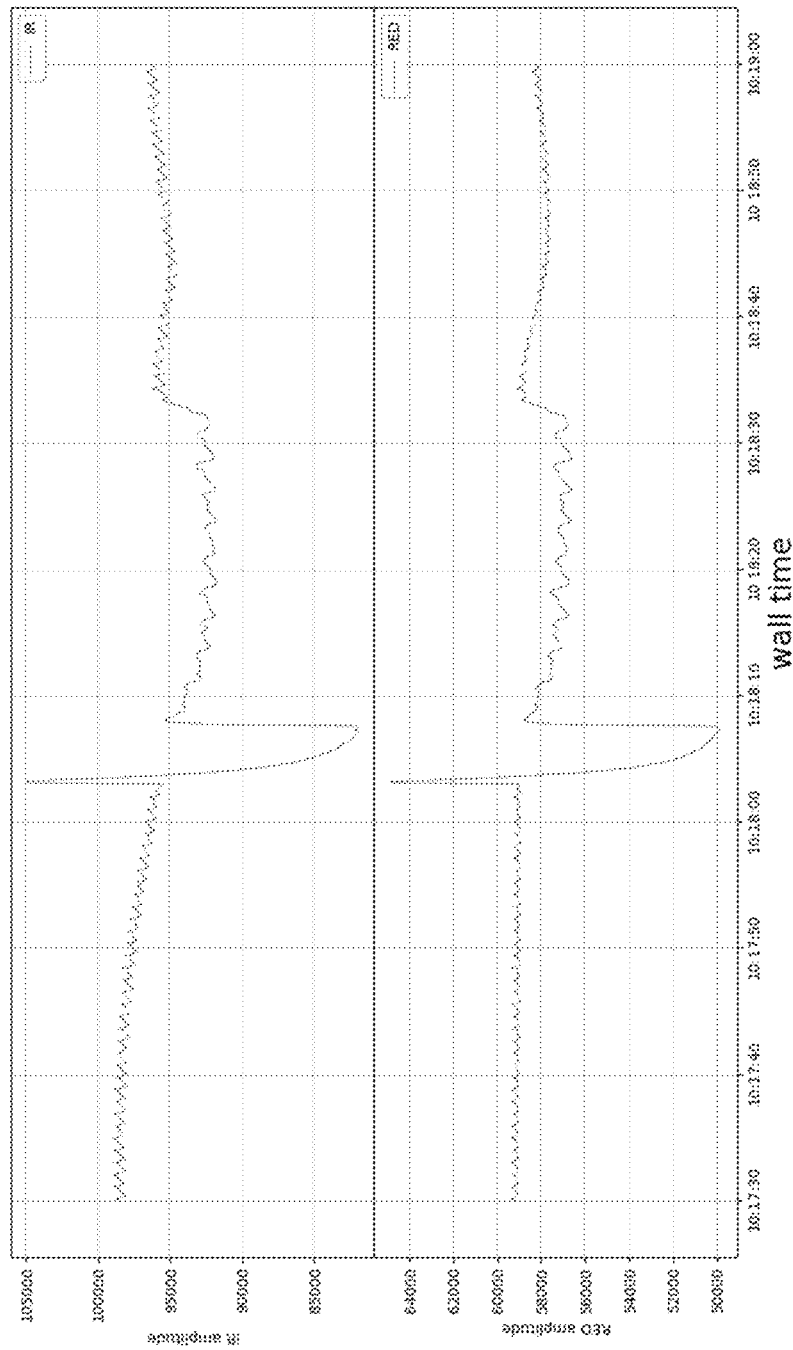
FIG. 17B is a plot of optical backscatter data vs time collected during study visit 3 of clinical testing during a period in which the blood flow rate was reduced from the patient's prescribed blood flow rate to 135 ml/min, in accordance with embodiment(s) of the present disclosure.
Figure 17C:
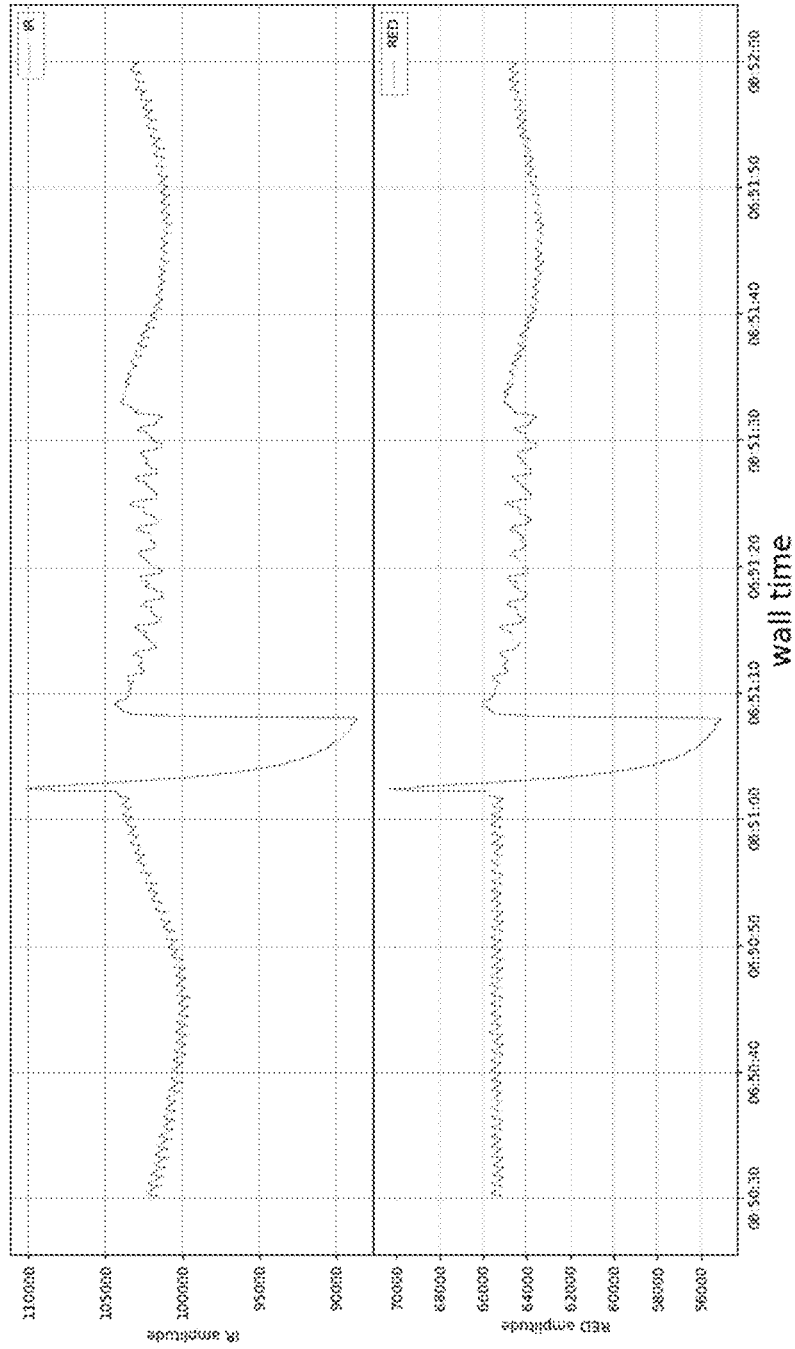
FIG. 17C is a plot of optical backscatter data vs time collected during study visit 3 of clinical testing during a period in which the blood flow rate was reduced from the patient's prescribed blood flow rate to 170 ml/min, in accordance with embodiment(s) of the present disclosure.
Figure 17D:
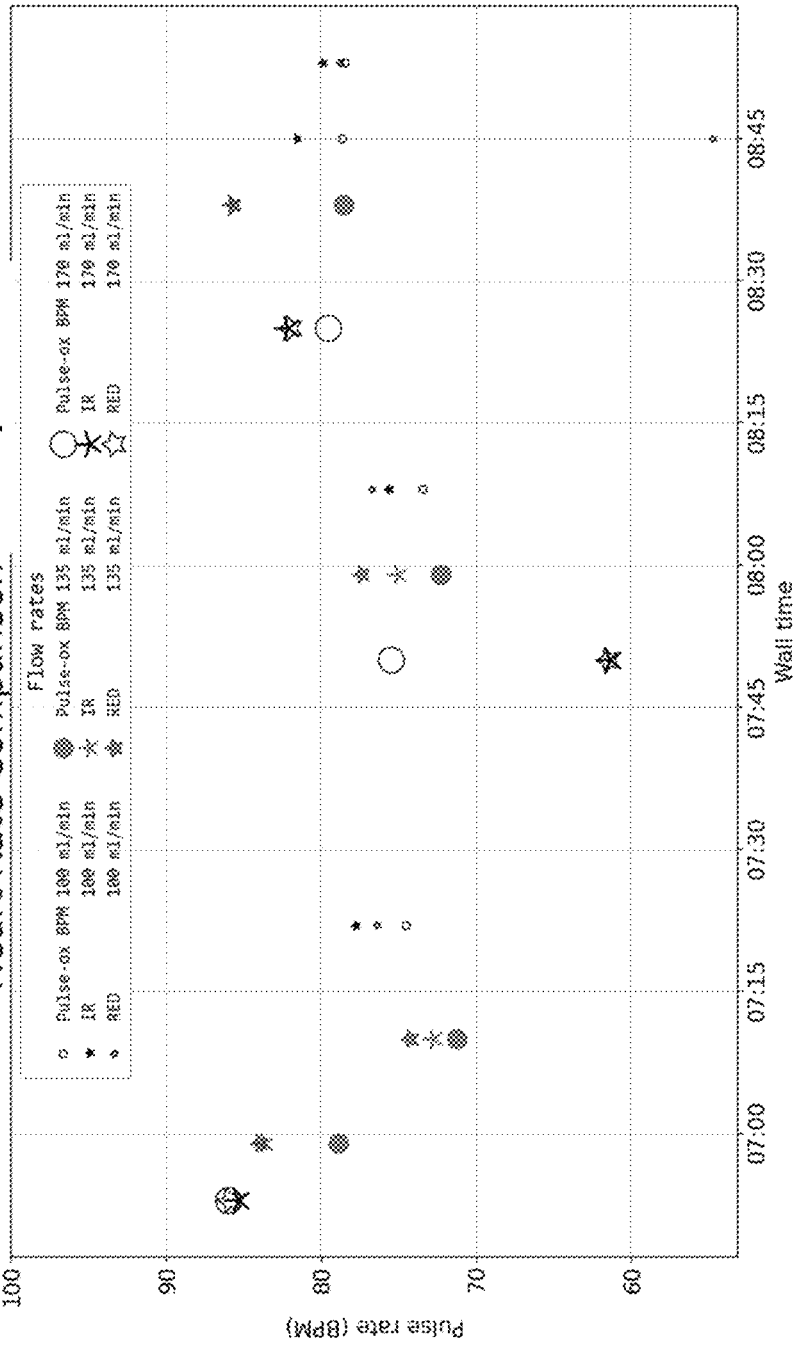
FIG. 17D is a plot of pulse rate versus time which includes the pulse rate of the pulse-ox and the pulse rate calculated based on the optical backscatter data from study visit 3, in accordance with embodiment(s) of the present disclosure.

FIG. 17A is a plot of a portion of the optical backscatter data (IR and Red) from another study visit (study visit 3), during a period when the blood flow rate was reduced from the patient's prescribed rate to 100 ml/min for about 30 seconds. FIG. 17B is a plot of another portion of the optical backscatter data (IR and Red) from the same study visit (study visit 3), during a period when the blood flow rate was reduced from the patient's prescribed rate to 135 ml/min. FIG. 17C is a plot of another portion of the optical backscatter data (IR and Red) from the same study visit (study visit 3), during a period when the blood flow rate was reduced from the patient's prescribed rate to 170 ml/min. The patient's prescribed blood flow rate for study visit 3 was 450 ml/min, but for portions of the treatment was reduced lower (e.g., 350 ml/min) and the patient's access was an arteriovenous graft. During this study visit, the blood flow rate was reduced a total 11 times, 4 times it was reduced to 100 ml/min, 4 times it was reduced to 135 ml/min, and 4 times it was reduced to 170 ml/min. The optical backscatter plots for study visit 3 show sharp drops and rises in the optical backscatter value at the start of the 30 second reduced blood flow rate periods, which was not seen in study visit 1 or study visit 2. The reason for this difference is during study visit 3 dropping the blood flow rate to the reduced rates (i.e., 100, 135 and 170 ml/min) triggered TMP alarms that stopped the blood pump, but in each case, it was restarted to the reduced blood flow rate. The optical backscatter data during these periods of reduced blood flow rate was then analyzed (e.g., utilizing process 700) to verify the presence and calculate a heart rate for the patient. FIG. 17D is a plot showing the calculated heart rate for the patient during each of these periods of reduced blood flow rate along with the heart rate measured simultaneously by the pulse-ox.

As illustrated by FIGS. 15D, 16D, and 17D, the calculated heart rate for the patient tracked fairly accurately to the heart rate measured by the pulse-ox. This demonstrates the capability of the optical backscatter data to be utilized to verify the presence (or absence) of a heartbeat/heartrate to confirm whether an actual needle dislodgement event has occurred, and also the capability to monitor the heart rate of the patient by analyzing the optical backscatter data.

Figure 18:
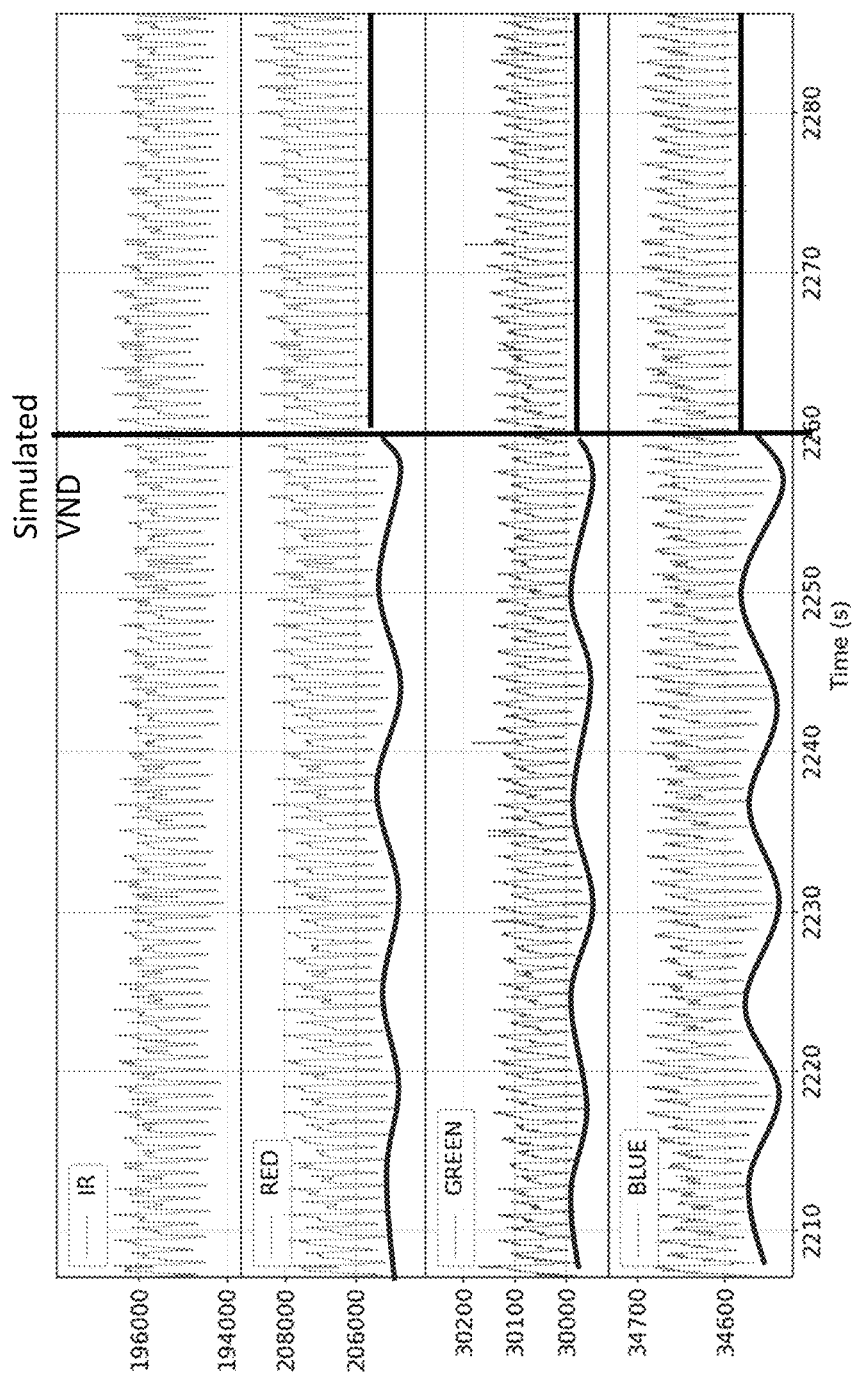
FIG. 18 is a plot of optical backscatter data (IR, red, green, and blue) vs time collected during lab testing at a blood flow rate of 420 mL/min during which a venous needle dislodgement was simulated, in accordance with embodiment(s) of the present disclosure.

FIG. 18 is a plot of optical backscatter data (IR, red, green, and blue) vs. time collected during lab testing using an extracorporeal circuit setup, dialysis machine operating at a blood flow rate of 420 mL/min, and a pump to simulate a patient's heartbeat (70 bpm), during which a venous needle dislodgement of the extracorporeal circuit was simulated (i.e., at about time 2260). As illustrated in FIG. 18 via the dotted lines, prior to the simulated VND, there is visible oscillation in the signal valleys, which changes (e.g., ends or decreases considerably) following the simulated VND. This oscillation in the signal valleys can be indicative of the simulated heartbeat, and the system and methods (e.g., process 700) described herein can be used to identify and calculate the heartrate and/or identify the loss or absence of a heartbeat, to identify and/or confirm a venous needle dislodgement while operating at a full prescribed blood flow rate (i.e., without first reducing the blood pump speed).

Terms used herein should be accorded their ordinary meaning in the relevant arts, or the meaning indicated by their use in context, but if an express definition is provided, that meaning controls.

Herein, references to "one embodiment", "an embodiment", "one implementation", or "an implementation" do not necessarily refer to the same embodiment or implementation, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to one or multiple ones. Additionally, the words "herein," "above," "below" and words of similar import, when used in this application, refer to this application as a whole and not to any portions of this application. When the claims use the word "or" in reference to a list of two or more items, that word covers all the following interpretations of the word: any of the items in the list, all the items in the list and any combination of the items in the list, unless expressly limited to one or the other. In this description, it is understood that terms such as "first," "second," "top," "bottom," "up," "down," and the like, are words of convenience and are not to be construed as limiting terms unless specifically stated to the contrary. Any terms not expressly defined herein have their conventional meaning as commonly understood by those having skill in the relevant art(s).

All documents mentioned herein are hereby incorporated by reference in their entirety. References to items in the singular should be understood to include items in the plural, and vice versa, unless explicitly stated otherwise or clear from the text.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately" or the like, when accompanying a numerical value, are to be construed as indicating a deviation as would be appreciated by one of ordinary skill in the art to operate satisfactorily for an intended purpose. For example, the term "about" as used herein may denote a variation of at most 10% around a numerical value. Further, RED refers to light with wavelengths in a range of about 620 nm to about 750 nm, e.g., about 700 nm. Green refers to light with wavelengths in a range of about 495-570 nm, e.g., about 525 nm. Blue refers to light with wavelengths in a range of about 450 to 495 nm, e.g., about 475 nm. IR refers to radiation with wavelengths in a range of about 780 nm to about 1,000 microns, e.g., in a range of about 780 nm to about 2500 nm (near infrared), or in a range of about 2.5 microns to about 50 microns (middle infrared), or in a range of about 50 microns to about 1000 microns (far infrared). Similarly, words of approximation such as "about," "approximately," or "substantially" when used in reference to physical characteristics, should be understood to contemplate a range of deviations that would be appreciated by one of ordinary skill in the art to operate satisfactorily for a corresponding use, function, purpose, or the like. Ranges of values and/or numeric values are provided herein as examples only, and do not constitute a limitation on the scope of the described embodiments. Where ranges of values are provided, they are also intended to include each value within the range as if set forth individually, unless expressly stated to the contrary. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

What is claimed is:

1. A method of monitoring an extracorporeal blood circuit of a patient and identifying a needle dislodgement, the method comprising:
   identifying a potential needle dislodgement event based on changes in pressure of the extracorporeal blood circuit;
   searching for a heart rate of a patient by analyzing an optical backscatter signal from an optical sensor attached to the extracorporeal blood circuit; and
   verifying the potential needle dislodgement event is a needle dislodgement based on the absence of the heart rate.

2. The method of claim 1, wherein the potential needle dislodgement event is identified by an algorithm that calculates a needle dislodgement value based on a maximum arterial pressure difference, a venous pressure change, the arterial pressure, and the venous pressure, and when the needle dislodgement value is below a threshold value the algorithm identifies the potential needle dislodgement event.

3. The method of claim 1, wherein the heart rate of the patient is searched for using an algorithm that analyzes the optical backscatter signal by:

filtering data from the optical backscatter signal to produce filtered optical backscatter data (FOBD);

computing a peak to peak (PTP) value by subtracting min FOBD from max FOBD;

computing a prominence value based on PTP value;

identifying and indexing peaks from the FOBD with a prominence above a prominence threshold (PT) and a distance between each peak above a minimum peak distance (min PD);

calculating peak times when more than one peak is indexed; and calculating the heart rate based on the peak times.

4. The method of claim 3, further comprising verifying the potential needle dislodgement event is not a needle dislodgement based on the presence of the heart rate (HR) within a set HR range, a variance of the FOBD within a set variance range, and a blood pump rate (BPR) within a set BPR range.

5. The method of claim 4, further comprising identifying an arterial heart rate of the patient by analyzing changes in the arterial pressure of the extracorporeal blood circuit, wherein the set HR range is determined based on the identified arterial heart rate.

6. The method of claim 5, wherein verifying the potential needle dislodgement event is further based on the presence of the arterial heart rate with a set arterial HR range.

7. The method of claim 1, wherein the optical sensor is attached to a venous line of the extracorporeal blood circuit and the needle dislodgement is a venous needle dislodgement.

8. A system for detecting a needle dislodgement of an extracorporeal blood circuit of a patient, the system comprising:
   a computing device;
   a processor;
   a memory comprising instructions, when executed by the processor cause the system to:
      receive a venous pressure signal, an arterial pressure signal, and an optical backscatter signal from an optical sensor attached to a venous line of the extracorporeal blood circuit;
      identify a potential needle dislodgement event based on changes in the arterial pressure signal and the venous pressure signal;
      search for a heart rate of the patient by analyzing the optical backscatter signal; and
      verify the potential needle dislodgement event is a needle dislodgement based on the absence of the heart rate.

9. The system of claim 8, wherein the memory comprising instructions, when executed by the processor cause the system to:
   reduce a speed of a blood pump for the extracorporeal blood circuit when the potential needle dislodgement event is identified; and
   search for the heart rate of the patient while the blood pump is at the reduced speed.

10. The system of claim 9, wherein the speed of the blood pump is reduced to a blood flow rate between about 50-120 mL/min when the potential needle dislodgement event is identified.

11. The system of claim 9, wherein the memory comprising instructions, when executed by the processor cause the system to verify the potential needle dislodgement event is not a needle dislodgement based on the presence of the heart rate.

12. The system of claim 11, wherein the memory comprising instructions, when executed by the processor cause the system to return the blood pump to a previous speed following verification that the potential needle dislodgement event is not a needle dislodgement.

13. The system of claim 8, wherein the memory comprising instructions, when executed by the processor cause an algorithm to calculate a needle dislodgement value based on a maximum arterial pressure difference, a venous pressure change, an arterial pressure, and a venous pressure, and when the needle dislodgement value is below a threshold value the algorithm identifies the potential needle dislodgement event.

14. The system of claim 8, wherein the memory comprising instructions, when executed by the processor cause an algorithm to search for the heart rate of the patient by analyzing the optical backscatter signal, the steps of the algorithm comprise:
   filtering data from optical backscatter signal to produce filtered optical backscatter data (FOBD);
   computing a peak to peak (PTP) value by subtracting min FOBD from max FOBD;
   computing a prominence value based on PTP value;
   identifying and indexing peaks from the FOBD with a prominence above a prominence threshold (PT) and a distance between each peak above a minimum peak distance (min PD);
   calculating peak times when more than one peak is indexed; and
   calculating the heart rate based on the peak times.

15. The system of claim 14, wherein the memory comprising instructions, when executed by the processor, cause the system to verify the potential needle dislodgement event is not a needle dislodgement based on the presence of the heart rate (HR) within a set HR range, a variance of the FOBD within a set variance range, and a blood pump rate (BPR) within a set BPR range.

16. A dialysis machine, comprising:
   a blood pump;
   an extracorporeal blood circuit configured to connect the blood pump and a dialyzer to a patient;
   an arterial pressure monitor and a venous pressure monitor;
   an optical sensor attached to a venous line of the extracorporeal blood circuit;
   a computing device comprising a processor and a memory, the computing device being configured to:
      receive a venous pressure signal from the venous pressure monitor, an arterial pressure signal from the arterial pressure monitor, and an optical backscatter signal from the optical sensor;
      identify a potential needle dislodgement event based on changes in the arterial pressure and venous pressure;
      search for a heart rate of a patient by analyzing the optical backscatter signal; and
      verify the potential needle dislodgement event is a needle dislodgement based on the absence of the heart rate.

* * * * *